(12) United States Patent
Parmer et al.

(10) Patent No.: US 8,192,445 B2
(45) Date of Patent: Jun. 5, 2012

(54) TRAJECTORY GUIDE WITH INSTRUMENT IMMOBILIZER

(75) Inventors: Kari Parmer, Melbourne, FL (US);
Thomas I. Miller, Palm Bay, FL (US);
John David, Malabar, FL (US)

(73) Assignee: Medtronic, Inc., Minneapolis, MA (US)

(*) Notice: Subject to any disclaimer, the term of this patent is extended or adjusted under 35 U.S.C. 154(b) by 162 days.

(21) Appl. No.: 12/620,399

(22) Filed: Nov. 17, 2009

(65) Prior Publication Data

US 2010/0063516 A1 Mar. 11, 2010

Related U.S. Application Data

(62) Division of application No. 10/894,958, filed on Jul. 20, 2004, now Pat. No. 7,637,915, which is a division of application No. 09/932,141, filed on Aug. 17, 2001, now Pat. No. 6,902,569.

(60) Provisional application No. 60/225,952, filed on Aug. 17, 2000.

(51) Int. Cl.
*A61B 19/00* (2006.01)

(52) U.S. Cl. ........... 606/130; 606/129; 606/96; 600/426

(58) Field of Classification Search ........... 606/130, 606/129, 53, 56, 59, 72, 79, 80, 8, 102; 600/424, 600/426, 429
See application file for complete search history.

(56) References Cited

U.S. PATENT DOCUMENTS

| | | |
|---|---|---|
| 431,187 A | 7/1890 | Foster |
| 438,801 A | 10/1890 | Delehanty |
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |

(Continued)

FOREIGN PATENT DOCUMENTS

DE 3108766 9/1982

(Continued)

OTHER PUBLICATIONS

"Fathom Remote Introducer", Image-Guided Neurologics, Inc., CNS Hynes Convention, Center, 2p., (Oct. 30-Nov. 4, 1999).

(Continued)

*Primary Examiner* — Tuan Nguyen

(74) *Attorney, Agent, or Firm* — Scott A. Marks; Harness Dickey Pierce PLC

(57) ABSTRACT

A trajectory guide assembly that guides an instrument relative to a patient includes a mounting seat configured to be supported by the patient. The assembly also includes a trajectory member moveably supported by the mounting seat. The trajectory member defines a trajectory passage. Also, the assembly includes a cap member moveably supported by the trajectory member. The cap member defines a cap opening, and the cap member is selectively moveable to a first position relative to the trajectory member to retain the instrument in both the cap opening and the trajectory passage. Additionally, the cap member is selectively moveable to a second position relative to the trajectory member to release the instrument.

19 Claims, 35 Drawing Sheets

U.S. PATENT DOCUMENTS

| | | |
|---|---|---|
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew et al. |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,026,276 A | 5/1977 | Chubbuck |
| 4,040,427 A | 8/1977 | Winnie |
| 4,131,257 A | 12/1978 | Sterling |
| 4,230,117 A | 10/1980 | Anichkov et al. |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen |
| 4,618,978 A | 10/1986 | Cosman |
| 4,629,451 A | 12/1986 | Winters et al. |
| 4,638,798 A | 1/1987 | Shelden et al. |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |
| 5,423,848 A | 6/1995 | Washizuka et al. |
| 5,445,166 A | 8/1995 | Taylor |
| 5,452,720 A | 9/1995 | Smith et al. |
| 5,464,446 A | 11/1995 | Dreessen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,618,288 A | 4/1997 | Calvo |

| | | | | | | |
|---|---|---|---|---|---|---|
| 5,622,170 | A | 4/1997 | Schulz | 6,457,963 B1 | 10/2002 | Tawara et al. |
| 5,638,819 | A | 6/1997 | Manwaring et al. | 6,482,182 B1 | 11/2002 | Carroll et al. |
| 5,639,276 | A | 6/1997 | Weinstock et al. | 6,488,620 B1 | 12/2002 | Segermark et al. |
| 5,643,286 | A | 7/1997 | Warner et al. | 6,491,699 B1 | 12/2002 | Henderson et al. |
| 5,647,361 | A | 7/1997 | Damadian | 6,529,765 B1 | 3/2003 | Franck et al. |
| 5,649,936 | A | 7/1997 | Real | 6,537,232 B1 | 3/2003 | Kucharczyk et al. |
| 5,658,272 | A | 8/1997 | Hasson | 6,546,277 B1 | 4/2003 | Franck et al. |
| 5,662,600 | A | 9/1997 | Watson et al. | 6,546,279 B1 | 4/2003 | Bova et al. |
| 5,667,514 | A | 9/1997 | Heller | 6,547,795 B2 | 4/2003 | Schneiderman |
| 5,695,501 | A | 12/1997 | Carol et al. | 6,556,857 B1 | 4/2003 | Estes et al. |
| 5,713,858 | A | 2/1998 | Heruth et al. | 6,609,020 B2 | 8/2003 | Gill |
| 5,755,697 | A | 5/1998 | Jones et al. | 6,610,100 B2 | 8/2003 | Phelps et al. |
| 5,776,064 | A | 7/1998 | Kalfas et al. | 6,632,184 B1 | 10/2003 | Truwit |
| 5,776,143 | A | 7/1998 | Adams | 6,655,014 B1 | 12/2003 | Babini |
| 5,776,144 | A | 7/1998 | Leysieffer et al. | 6,662,035 B2 | 12/2003 | Sochor |
| 5,788,713 | A | 8/1998 | Dubach et al. | 6,676,669 B2 | 1/2004 | Charles et al. |
| 5,807,033 | A | 9/1998 | Benway | 6,706,050 B1 | 3/2004 | Giannadakis |
| 5,809,694 | A | 9/1998 | Postans et al. | 6,726,678 B1 | 4/2004 | Nelson et al. |
| 5,810,712 | A | 9/1998 | Dunn | 6,746,471 B2 | 6/2004 | Mortier et al. |
| 5,817,106 | A | 10/1998 | Real | 6,752,812 B1 | 6/2004 | Truwit |
| 5,823,975 | A | 10/1998 | Stark et al. | 6,765,122 B1 | 7/2004 | Stout |
| 5,833,627 | A | 11/1998 | Shmulewitz et al. | 6,773,443 B2 | 8/2004 | Truwit et al. |
| 5,843,150 | A | 12/1998 | Dreessen et al. | 6,782,288 B2 | 8/2004 | Truwit et al. |
| 5,851,183 | A | 12/1998 | Bucholz | 6,802,323 B1 | 10/2004 | Truwit et al. |
| 5,865,817 | A | 2/1999 | Moenning et al. | 6,902,569 B2 | 6/2005 | Parmer et al. |
| 5,865,842 | A | 2/1999 | Knuth et al. | 6,913,478 B2 | 7/2005 | Lamirey |
| 5,871,445 | A | 2/1999 | Bucholz | 6,944,895 B2 | 9/2005 | Truwit |
| 5,871,487 | A | 2/1999 | Warner et al. | 6,960,216 B2 | 11/2005 | Kolb et al. |
| 5,873,822 | A | 2/1999 | Ferre et al. | 7,204,840 B2 | 4/2007 | Skakoon et al. |
| 5,891,034 | A | 4/1999 | Bucholz | 7,366,561 B2 | 4/2008 | Mills et al. |
| 5,891,157 | A | 4/1999 | Day et al. | 7,479,146 B2 | 1/2009 | Malinowski |
| 5,927,277 | A | 7/1999 | Baudino et al. | 7,637,915 B2 * | 12/2009 | Parmer et al. .............. 606/108 |
| 5,950,629 | A | 9/1999 | Taylor et al. | 2001/0014771 A1 | 8/2001 | Truwit et al. |
| 5,954,687 | A | 9/1999 | Baudino | 2001/0027271 A1 | 10/2001 | Franck et al. |
| 5,957,933 | A | 9/1999 | Yanof et al. | 2001/0037524 A1 | 11/2001 | Truwit |
| 5,957,934 | A | 9/1999 | Rapoport et al. | 2002/0010479 A1 | 1/2002 | Skakoon et al. |
| 5,964,705 | A | 10/1999 | Truwit et al. | 2002/0019641 A1 | 2/2002 | Truwit |
| 5,980,535 | A | 11/1999 | Barnett et al. | 2002/0022847 A1 | 2/2002 | Ray et al. |
| 5,984,930 | A | 11/1999 | Maciunas et al. | 2002/0052610 A1 | 5/2002 | Skakoon et al. |
| 5,993,463 | A * | 11/1999 | Truwit .............. 606/130 | 2002/0077646 A1 | 6/2002 | Truwit et al. |
| 5,997,471 | A | 12/1999 | Gumb et al. | 2002/0156372 A1 | 10/2002 | Skakoon et al. |
| 6,006,126 | A | 12/1999 | Cosman | 2003/0079287 A1 | 5/2003 | Truwit |
| 6,018,094 | A | 1/2000 | Fox | 2003/0187351 A1 | 10/2003 | Franck et al. |
| 6,021,343 | A | 2/2000 | Foley et al. | 2003/0208122 A1 | 11/2003 | Melkent et al. |
| 6,024,729 | A | 2/2000 | Dehdashtian et al. | 2004/0026161 A1 | 2/2004 | Takatsuka et al. |
| 6,030,223 | A | 2/2000 | Sugimori | 2004/0059260 A1 | 3/2004 | Truwit |
| 6,039,725 | A | 3/2000 | Moenning et al. | 2004/0176750 A1 | 9/2004 | Nelson et al. |
| 6,042,540 | A | 3/2000 | Johnston et al. | 2004/0243147 A1 | 12/2004 | Lipow |
| 6,044,304 | A | 3/2000 | Baudino | 2004/0255991 A1 | 12/2004 | Truwit et al. |
| 6,058,323 | A | 5/2000 | Lemelson | 2004/0260323 A1 | 12/2004 | Truwit et al. |
| 6,071,288 | A | 6/2000 | Carol et al. | 2004/0267284 A1 | 12/2004 | Parmer et al. |
| 6,076,008 | A | 6/2000 | Bucholz | 2006/0122627 A1 | 6/2006 | Miller et al. |
| 6,079,681 | A | 6/2000 | Stern et al. | 2006/0192319 A1 | 8/2006 | Solar |
| 6,110,182 | A | 8/2000 | Mowlai-Ashtiani | 2006/0195119 A1 | 8/2006 | Mazzocchi et al. |
| 6,117,143 | A | 9/2000 | Hynes et al. | 2007/0250078 A1 | 10/2007 | Stuart |
| 6,120,465 | A | 9/2000 | Guthrie et al. | 2007/0299427 A1 | 12/2007 | Yeung et al. |
| 6,135,946 | A | 10/2000 | Konen et al. | 2008/0004632 A1 | 1/2008 | Sutherland et al. |
| 6,179,826 | B1 | 1/2001 | Aebischer et al. | | | |
| 6,195,577 | B1 | 2/2001 | Truwit et al. | | | |
| 6,206,890 | B1 | 3/2001 | Truwit | | | |

FOREIGN PATENT DOCUMENTS

| | | |
|---|---|---|
| DE | 3937052 | 5/1990 |
| DE | 19726141 | 1/1999 |
| DE | 29612100 | 8/1999 |
| DE | 19808220 | 9/1999 |
| DE | 19820808 | 9/1999 |
| DE | 19826078 | 11/1999 |
| EP | 0386936 | 5/1990 |
| EP | 0427358 | 5/1991 |
| EP | 0724865 | 5/1991 |
| EP | 0609085 | 8/1994 |
| EP | 0832611 | 4/1998 |
| EP | 0904741 | 3/1999 |
| GB | 2237993 | 5/1991 |
| GB | 2329473 | 4/1998 |
| GB | 2346573 | 8/2000 |
| WO | WO-8809151 | 12/1988 |
| WO | WO-9721380 | 12/1988 |
| WO | WO-9522297 | 8/1995 |
| WO | WO-9610368 | 4/1996 |
| WO | WO-9633766 | 10/1996 |

| | | | | |
|---|---|---|---|---|
| 6,210,417 | B1 | 4/2001 | Baudino et al. | |
| 6,231,526 | B1 | 5/2001 | Taylor et al. | |
| 6,236,875 | B1 | 5/2001 | Bucholz et al. | |
| 6,238,402 | B1 | 5/2001 | Sullivan, III et al. | |
| 6,254,532 | B1 | 7/2001 | Paolitto et al. | |
| 6,257,407 | B1 | 7/2001 | Truwit et al. | |
| 6,261,300 | B1 | 7/2001 | Carol et al. | |
| 6,267,769 | B1 | 7/2001 | Truwit | |
| 6,267,770 | B1 | 7/2001 | Truwit | |
| 6,273,896 | B1 | 8/2001 | Franck et al. | |
| 6,282,437 | B1 | 8/2001 | Franck et al. | |
| 6,290,644 | B1 | 9/2001 | Green, II et al. | |
| 6,298,262 | B1 | 10/2001 | Franck et al. | |
| 6,315,770 | B1 | 11/2001 | de la Torre et al. | |
| 6,321,104 | B1 | 11/2001 | Gielen et al. | |
| 6,327,491 | B1 | 12/2001 | Franklin et al. | |
| 6,356,792 | B1 | 3/2002 | Errico et al. | |
| 6,368,329 | B1 | 4/2002 | Truwit | |
| 6,400,992 | B1 | 6/2002 | Borgersen et al. | |

| WO | WO-9703609 | 2/1997 |
| --- | --- | --- |
| WO | WO-9742870 | 11/1997 |
| WO | WO-9817191 | 4/1998 |
| WO | WO-9825535 | 6/1998 |
| WO | WO-9851229 | 11/1998 |
| WO | WO-0001316 | 1/2000 |
| WO | WO-0018306 | 1/2000 |
| WO | WO-0124709 | 4/2001 |
| WO | WO-0149197 | 7/2001 |
| WO | WO-0176498 | 7/2001 |
| WO | WO-2004026161 A2 | 4/2004 |

OTHER PUBLICATIONS

"Inomed Competence in Neurophysologic Monitoring", http://www.inomed.com/english/index.htm, (observed Mar. 23, 2004), 2 pgs.

"MicroTargeting® Precision Guidance Using Microelectrode Recording", (Aug. 15, 2003), 5 pgs.

"Possible Existence of Common Internalization Mechanisms among Arginine-rich Peptides", Suzuki, T. et al., Journal of Biological Chemistry, vol. 277, No. 4 (2002) pp. 2437-2443.

Allison, S., et al., "Microchannel Plate Intensifier Response in Traverse Magnetic Field", Electronic Letters, 26, (Jun. 7, 1990), 770-771.

Drake, J.M., et al. "ISG Viewing Wand System", Neurosurgery, 34 (6), (Jun. 1994), 1094-1097.

Dyer, P.V., et al., "The ISG Viewing Wand: an Application to Atlanto-Axial Cervical Surgery Using the Le For I Maxillary Osteotomy", British Journal of Oral and Maxillofacial Surgery, 33, (1995), 370-374.

Franck Joel, et al., "microTargeting® Platform System incorporating StarFix™ guidance", microTargeting, pp. 1-44.

Franck, Joel, et al., "microTargeting® Platform incorporating StarFix™ guidance", *microTargeting*, 3 pgs.

Gehring, W. J., "Homeodomain Proteins", Annu. Rev. Biochem., vol. 63 (1997) pp. 487-526.

Gillies, G., et al., "Magnetic Manipulation Instrumentation for Medical Physics Research", Review of Scientific Instruments, 65 (3), Review Article, (Mar. 1994), 533-562.

Grady, M., "Nonlinear Magnetic Stereotaxis:Three-Dimensional, in vivo Remote Magnetic Manipulation of a Small Object in Canine Brain", Medical Physics, 17 (3), (May/Jun. 1990), pp. 405-415.

Grady, M., et al., "Initial Experimental Results of a New Stereotaxic Hyperthermia System", American College of Surgeons; 1998 Clinical Congress: Surgical Forum, 39, (1998), 507-509.

Grady, M., et al., "Magnetic Stereotaxis System for Neurosurgical Procedures", Proc. 37th International Instrumentation Symp., Sand Diego, CA (May 1991), 665-675.

Grady, M., et al., "Magnetic Stereotaxis: A Technique to Deliver Stereotactic Hyperthermia", Neurosurgery, 27 (6), Technical Note, (Dec. 1990), pp. 1010-1016.

Grady, M., et al., "Preliminary Experimental Investigation of in vivo Magnetic Manipulation: Results and Potential Application in Hyperthermia", medical Physics, 16 (2), (Mar./Apr. 1989), pp. 263-272.

Hata, N., et al., "Needle Insertion Manipulator for CT-and MR-Guided Stereotactic Neurosurgery", Interventional MR:Techniques and Clinical Experience, St. Louis: London: Mosby; Martin Dunitz, F. Jolesz and I. Young, eds., (1998), 99-106.

Hirschberg, H., et al., "Image-Guided Neurosurgery—MR compatible stereotactic equipment", http:www.medinnova.no/English/P51466ster.html. (Mar. 29, 2001), 1p.

Hirschberg, Henry, et al., "Image-guided neurosurgery", stereotactic equipment for MR imaging, http://www.medinnova.no/English/P51466ster.html, (Observed Mar. 8, 2002), 1 page.

Howard, M. et al. "Magnetc Movement of a Brain Thermocepter", Neurosugery, 24 (3), (1989), 444-448.

Howard, M., et al., "Magnetic Neurosurgery", Stereotactic and Functional Neurosurgery, 66, (1996), 102-107.

Howard, M., et al., "Magnetic Neurosurgery: Image-Guided, Remote-Controlled Movement of Neurosurgical Implants", Ch. 26 in: Clinical Neurosurgery: Proceedings of the Congress of Neurological Surgeons, San Francisco, CA, (1995), 382-391.

Howard, M., et al., "Review of Magnetic Neurosurgery Research", Image Guided Surgery, 1, (Nov. 1995), 295-299.

International Search Report and Written Opinion for PCT/US05/43651 mailed May 8, 2008.

Lawson, M., et al. "Near Real-Time Bi-planar Fluoroscopic Tracking System for the Video Tumor Fighter", SPIE, 1445, (1991), 265-275.

Leggett, W.B., et al. "Surgical Technology—The Viewing Wand: A New System for Three-Dimensional Computed Tomography-Correlated Intraoperative Localization", Current Surgery, (Dec. 1991), 674-678.

Malison, R.T., et al., "Computer-Assisted Coregistration of Multislice SPECT and MR Brain Ilmages by Fixed External Fiducials", Journal of Computer Assisted Tomography. 17 (6), (1993), pp. 952-960.

Mannervik, M., "Target genes of homeodomain proteins", BioEssays vol. 21.4 (Apr. 1999) pp. 267-270.

McNeil., R., et al., "Characteristics of an Improved Magnetic-Implant Guidance System", IEEE Transactions on Biomedical Engineering, 42 (8), (Aug. 1995), 802-808.

McNeil., R., et al., "Functional Design Features and Initial Performance Characteristics of a Magnetic-Implant Guidance System for Stereotactic Neurosurgery", IEEE Transactions on Biomedical Engineering, 42 (8), (1995), 793-801.

Meeker, D., et al., "Optimal Realization of Arbitrary Forces in a Magnetic Stereotaxis System," IEEE Transactions on Magnetics, 32 (2), (Mar. 1996), 320-328.

Molloy, J., et al., "Experimental Determination of the Force Required for Insertion of a Thermoseed into Deep Brain Tissues", Annals of Biomedical Engineering, 18, (1990), 299-313.

Molly, J., et al., "Thermodynamics of Movable Inductively Heated Seeds for the Treatment of Brain Tumors", Medical Physics, 18 (4), (1991), 794-803.

Oliver, L., "Cup-And-Ball Chemopallidectomy Apparatus", (1958), p. 401.

Patikoglou, G. et al., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P., et al., "Electro-Optic Imaging Chain or a Biplanar Fluoroscope for Neurosurgery: Magnetic Field Sensitivity and Contrast Measurements", Optical Engineering 32, (7), (1993), 1644-1656.

Ramos, P., et al., "Low-Dose, Magnetic Field-Immune, Bi-Planar Fluoroscopy for Neurosurgery", Proc. SPIE, 1443 (Medical Imaging V: Image Physics), (1991), 160-170.

Ramos, P. et al. "Microchannel Plate Image Intensifier Electron Dynamics in Magnetic Field", Electronics Letters, 27 (18), (Aug. 29, 1991), pp. 1636-1638.

Ritter, R., et al., "Magnetic Stereotaxis: Computer-Assisted, Image-Guided Remote Movement of Implants in the Brain", Ch. 26 in: Computer-Integrated Technology and Clinical Applications, MIT Press, Cambridge, MA., Taylor, R., et al., eds., (1996), 363-369.

Ritter, R., et al., "Magnetic Sterotaxis: An Application of Magnetic Control Technology to the Needs of Clinical Medicine", Proc. of the MAG'95 Industrial Conf. and Exhibition, Technomic Pub. Co., Lancaster, PA., Allaire, P., ed., (1995), 186-193.

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

Sandeman, D.S., et al., "Advances in image-directed neurosurgery: Preliminary experience with the ISG Viewing Wand compared with the Leksell G frame", British Journal of Neurosurgery, 8 (199), pp. 529-544.

Stein, S. et al., "Checklist: Vertebrate homeobox genes", Mechanisms of Development, vol. 55, No. 1 (Mar. 1996) pp. 91-108.

Supplementary European Search Report mailed Oct. 26, 2009 for EP05852969 filed Dec. 6, 2005 claiming benefit of U.S. Appl. No. 11/005,907, filed Dec. 5, 2004.

Szikora, I., et al., "Endovascular Treatment of Experimental Aneurysms with Liquid Polymers: The Protective Potential of Stents", Neurosurgery, 38, (Feb. 1996), 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

Yeh, H.S., et al., "Implantation of intracerebral depth electrodes for monitoring seizures using the Pelorus stereotactic system guided by magnetic resonance imaging", J. Neurosurg., 78 (1993), pp. 138-141.

Zinreich, S.J., et al., "Frameless Sterotaxic Integration of CT Imaging Data: Accuracy and Initial Applications", Radiology, 188 (3), (1993), pp. 735-742.

European Office Action mailed Jan. 22, 2010 for European Application No. 05 852 969.4.

* cited by examiner

TRAJECTORY GUIDE WITH INSTRUMENT IMMOBILIZER

CROSS-REFERENCE TO RELATED APPLICATIONS

This application is a divisional application of U.S. patent application Ser. No. 10/894,958 (issued as U.S. Pat. No. 7,637,915), filed Jul. 20, 2004, which is a divisional application of U.S. patent application Ser. No. 09/932,141 (issued as U.S. Pat. No. 6,902,569), filed Aug. 17, 2001, which claims the benefit of priority to U.S. Provisional Patent Application Ser. No. 60/225,952, filed Aug. 17, 2000, the disclosures of which are incorporated herein by reference in their entirety.

FIELD

This document relates generally to surgical trajectory guides. More specifically, but not by way of limitation, it relates to apparatuses and methods that facilitate alignment of surgical and observational instruments into a body.

BACKGROUND

This section provides background information related to the present disclosure which is not necessarily prior art.

In the treatment of some diseases or defects associated with a patient, it has been found necessary to access specific targets within a patient. In the treatment of some diseases of or defects of human beings, it has been found necessary to access specific portions of the brain. Currently there are several methods for inserting surgical and observational instruments into a patient's brain.

U.S. Pat. No. 3,055,370 issued to McKinney et al. shows one currently used method for placing a surgical instrument to access a specific portion of the brain. The surgical instrument of the '370 patent includes a ball which has a bore. The direction of the bore can be changed. The instrument has an elongated tube of a specific length. A stylet is inserted within the tube to access the globus pallidus and perform a pallidotomy. An opening or burr hole is made in the skull at a specific landmark on the skull. Next, X-rays are taken in the fore-and-aft (AP) and lateral positions, and the line of the bar is projected downwardly by a ruler both in the fore-and-aft (AP) and lateral positions, so that the direction of the needle can be determined before it is inserted. When the direction of the longitudinal axis of the tubular member is determined to be satisfactory, a holder is threaded further into a tap to force a surface against a ball and lock a tubular member into place. Alignment of the trajectory is not measurable along a specific line occurring at the intersection of two planes. Alignment is dependent on placement of the burr hole at a specific location to determine one plane. X-rays are used to determine another plane-based use of common landmarks on the skull. The end result is that an educated guess is being used to position the stylet at the globus pallidus for the pallidotomy. One shortcoming with the method of using X-ray imaging to direct a surgical or observational instrument, is that many of the destinations within a patient are not viewable via X-ray. Another shortcoming relates to the slight shifting of intracranial contents, once a burr hole is placed and the dura and arachnoid are penetrated. Once cerebrospinal fluid is released via the burr hole, the intracranial contents (i.e. brain) may shift one or more millimeters. In such a case, the calculated trajectory is no longer accurate. Hence, there is an inherent inaccuracy with the described scheme.

Several other methods are also used to place instruments, catheters, or observational tools into patients. Currently, surgical procedures are performed through craniotomy flaps or craniotomy burr holes. A burr hole of about 14 mm is made in the skull. Needles or probes are typically passed through the burr hole into the brain using framed stereotaxy, frameless stereotaxy or freehand without stereotaxy.

The freehand method depends very heavily on the knowledge and judgment of the surgeon. In the freehand method, the surgeon determines the insertion point with a couple of measurements from a known landmark. The surgeon then looks at the measured point, makes adjustments, determines the angle of insertion and then inserts the surgical instrument or tool.

In framed stereotaxy, a ring frame is mounted to the patient's skull by multiple (typically three or four) pins or screws. This ring frame is used to determine a three dimensional data set. From this data set, Cartesian coordinates are calculated for both the lesion, the location of the pins or screws, and the fiducial marks on the frame. The ring frame fits into a large frame. A large frame is then attached to the patient in the operating suite. The large frame provides known positions and guides the surgical or observational instruments. The large frame is used to position the instrument to be introduced into the patient through a burr hole so that it intersects the target. In frameless stereotaxy, the ring frame is replaced with several markings on the patient's skull which can be used to determine several known positions. The large frame is replaced by a camera. The camera is usually infrared or some such device. Multiple sensors readable by the camera are placed on the instrument. For example, the surgical instrument or tool is provided with one or more light emitting diodes ("LEDs") which are tracked by the camera. The position of the surgical instrument can be calculated from the information from the LEDs on the surgical instrument or observational tool.

U.S. Pat. No. 4,955,891 and U.S. Pat. No. 4,805,615, both issued to Carol, each discuss the use of stereotaxy surgery with computerized tomographic ("CT") scanning. CT scanning is used to determine the exact position of a lesion or specific portion of the brain. After the exact position of the lesion or specific portion of the brain is determined, a phantom fixture is set up. The phantom fixture replicates the position of the ring frame on the patient. A phantom target is set up. The instrument can then be positioned on the phantom such that it intersects the target. The information from the phantom can then be used in actually positioning the instrument in the operating suite.

U.S. Pat. No. 4,998,938 issued to Ghajar et al. shows another surgical device for facilitating the insertion of an instrument into a patient's cranial cavity through a burr hole. The device includes a guide having an end configured to pass into the burr hole. There is a separate locking member. A body member includes alignment markings to help with insertion of a catheter or stylet. Unlike the '370 patent, there is no movable member for adjusting the path of the guide.

The methods currently in use all have a number of shortcomings. Most of the techniques currently used to place a surgical instrument or observational tool within a patient employ a limited amount of accuracy. In particular, current framed, frameless, and freehand methods compute or predict trajectories on the basis of imaging data or anatomic landmarks that do not account for the slight, but real shifting of the brain upon opening the cranium and meninges to the level of the subarachnoid space. This inherent inaccuracy inherently limits the success of these various methodologies. In other words, these systems do not use any means of updating the data files to include data obtained following the placement of a surgical burr hole and opening of the meninges. In addition, all the methods require large amounts of judgment on the part of the surgeon placing the surgical instrument or tool, and in particular, offer no direct feedback on the success or failure of the trajectory to reach the target. Very few of the techniques use an imaging or scanning apparatus to aid in the placement of the surgical instrument or observational tool. The only one that does requires a phantom frame and target to be set up to simulate the real geometry. In short, none of the apparatuses appear to use an imaging or scanning apparatus as extensively as they could be used to minimize the time and effort needed to accurately place a surgical instrument into a patient, and to offer immediate data on the success or failure of the trajectory to reach the target.

The trajectory guide system taught in Published International Patent Application PCT/US98/10008 (International Publication number WO 98/51229) addresses these and other shortcomings of prior art surgical working platform systems as described above. The disclosed system provides a means for accurately determining the trajectory of a surgical instrument within a passage which in turn lies within a guide or positioning stem that extends from a movable member that is selectably lockable in position with respect to a base. Some embodiments of this system employ removable guide stems or positioning stems that can be removed from the movable member once an appropriate trajectory has been chosen and a surgical instrument inserted into the passage formed within the chosen stem and movable member. One disadvantage of this system is that there may be axial movement introduced to the instrument by the process of removing the stem; that is, the instrument may be disadvantageously introduced further into the body, or disadvantageously removed farther from the body, by the axial motion of the stem as it is removed.

SUMMARY

This section provides a general summary of the disclosure, and is not a comprehensive disclosure of its full scope or all of its features.

A trajectory guide assembly that guides an instrument relative to a patient is disclosed. The assembly includes a mounting seat configured to be supported by the patient. The assembly also includes a trajectory member moveably supported by the mounting seat. The trajectory member defines a trajectory passage. Also, the assembly includes a cap member moveably supported by the trajectory member. The cap member defines a cap opening, and the cap member is selectively moveable to a first position relative to the trajectory member to retain the instrument in both the cap opening and the trajectory passage. Additionally, the cap member is selectively moveable to a second position relative to the trajectory member to release the instrument.

Also, a trajectory guide assembly that guides an instrument relative to a patient is disclosed. The trajectory guide assembly includes a mounting seat configured to be supported by the patient, and the mounting seat includes a hemispherical seat portion defining a seat opening passing therethrough. The assembly also includes a ball member rotatably supported within the hemispherical seat portion. The ball member defines a trajectory passage, and the trajectory passage and the seat opening are configured to simultaneously receive the instrument. Moreover, the assembly includes a cap member that is moveably supported by the ball member. The cap member defines a cap opening. Also, the cap member is selectively moveable to a first position relative to the ball member to retain the instrument in each of the cap opening, the trajectory passage, and the seat opening, and the cap member is selectively moveable to a second position relative to the ball member to release the instrument.

Still further, a method for guiding an instrument relative to a patient is disclosed that includes supporting a mounting seat on the patient and supporting a trajectory member on the mounting seat. The method also includes rotating the trajectory member relative to the mounting seat to point an axis of a trajectory passage toward a target in the patient. Furthermore, the method includes moving a cap member relative to the trajectory member to expose the trajectory passage through an opening in the cap member. Also, the method includes introducing the instrument through the opening in the cap member, the trajectory passage, and into the patient toward the target. Additionally, the method includes moving the cap member relative to the trajectory member to retain the instrument in both the opening and the trajectory passage and between the cap member and the trajectory member.

Moreover, a trajectory guide assembly that guides an instrument relative to a patient is disclosed. The trajectory guide assembly includes a mounting seat configured to be supported by the patient. The mounting seat includes a flange defining a hole that receives a fastener for selectively securing the mounting seat to the patient. The mounting seat further includes a hemispherical seat portion that defines a seat opening. The assembly also includes a spherical ball member rotatably supported within the hemispherical seat portion, and the ball member defines a trajectory passage. The trajectory passage has a width that is less than a width of the seat opening of the mounting seat. Furthermore, the assembly includes a first set screw that extends through the mounting seat and selectively secures the spherical ball member in a fixed position relative to the mounting seat. Moreover, the assembly includes a cap member that is slidably supported by the ball member, and the cap member defines a cap opening and a slot. The cap opening has a width that is less than a width of the trajectory passage. Additionally, the assembly includes a second set screw that is moveably received in the slot and that selectively secures the cap member in a fixed position relative to the ball member. The slot limits movement of the cap member relative to the ball member. Furthermore, the cap member is selectively moveable to a first position relative to the ball member to retain the instrument in each of the seat opening, the trajectory passage, and the cap opening and between the cap member and the trajectory member. Also, the cap member is selectively moveable to a second position relative to the ball member to release the instrument.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 9b and 9c are side and bottom views, respectively, of the cap member of FIG. 9a.

FIG. 10b is an exploded side view of the embodiment of FIG. 10a.

FIG. 12b is an isometric view illustrating the use of the alternative embodiment of FIG. 12a.

FIG. 13b is a top exploded view of a cap and the mounting seat and the movable member of FIG. 13a.

FIG. 14b is an exploded side view of the two-piece base of FIG. 14a.

FIG. 15b is a side view of the apparatus illustrated in FIG. 15a.

FIG. 16b is a side view of the mounting seat and collar of FIG. 16a.

FIG. 18b is a top view of the cap and mounting seat of FIG. 18a.

Corresponding reference numerals indicate corresponding parts throughout the several views of the drawings.

DETAILED DESCRIPTION

Example embodiments will now be described more fully with reference to the accompanying drawings.

This application incorporates International Patent Application PCT/US98/10008 (International Publication number WO 98/51229) by reference, together with the disclosure of its U.S. counterpart, issued U.S. Pat. No. 5,993,463, which is also incorporated herein by reference in its entirety.

Scanning System Example

Figure 1:
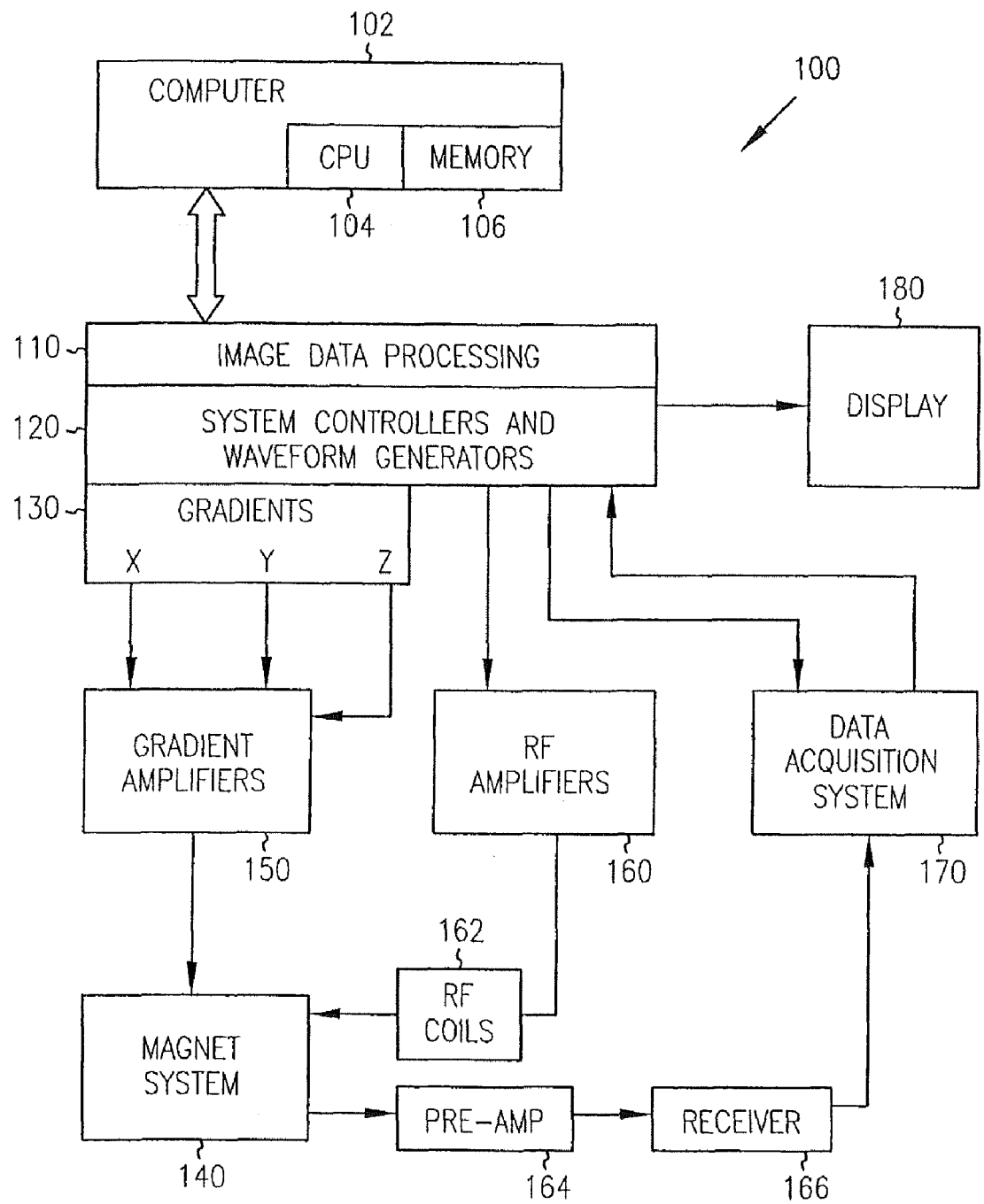
FIG. 1 is a block diagram of a patient scanning system.

FIG. 1 is a block diagram of a patient scanning system 100. The specific scanning system shown is for a magnetic resonance imaging ("MRI") system. An MRI scanning system 100 includes a computer 102. The computer 102 includes a central processing unit ("CPU") 104 and memory 106. The CPU 104 and memory 106 has the capacity to perform multiple calculations used to determine images as well as positions of various organs, or portions or within an image field. The computer 102 controls an image data processing portion 110, a system controller and waveform generator portion 120, and an XYZ gradient producing portion 130. The XYZ gradients are amplified and used to provide a gradient magnetic field in the X, Y, and Z directions as part of a magnet system 140. The magnet system 140 includes a magnet which produces a magnetic field through which a patient can pass. The shape of the magnet varies among MRI systems. The shape of the magnet and its relation to the table upon which the patient lies, determines whether the patient can be accessed by a surgeon while an MRI is being performed. There are many styles of MRI devices that do not place the surgeon within a close enough proximity to allow access to the patient during an MRI scan operation.

The MRI system 100 also includes gradient amplifier 150. Also included are a set of RF amplifiers 160 and RF coils 162 which are used in conjunction with the magnet system 140 to produce and transmit RF pulses in the magnetic field. Either the same RF coil or another RF coil is used to detect the MR signals from the interrogated tissues. This detected MR signal is then amplified by a preamplifier 164 and received by a receiver 166 for transmission to the data acquisition system 170 and then transmitted to the image data processing computer system 110. The data acquisition system is input to the system controllers and waveform generator portion 120 of the computer 102 as part of a feedback loop. The data is interpreted and placed on a display 180 associated with the computer of the MRI system 100. The computer 102 and the CPU 104 and memory 106 can use data acquired from the MRI system 100 to build up images of a portion of the patient which is being scanned. The images are typically referred to as slices. For example, a horizontal slice and a vertical slice can be made of the portion of the body or patient being imaged. The computer can also recalculate and build other slices for use by doctors and radiologists having any selected orientation needed to facilitate study of various items within a patient. For example, lesions can be found within the body as well as certain organs. Different slices can be requested to facilitate study of these targets. From the data acquired, the position of the lesions or organs can also be very accurately determined using a Cartesian or polar coordinate system. The above description of the MR scanner is simply for demonstrative purposes and multiple alternative MR scanning systems can be described herein.

Trajectory Guide Example

Figure 2:
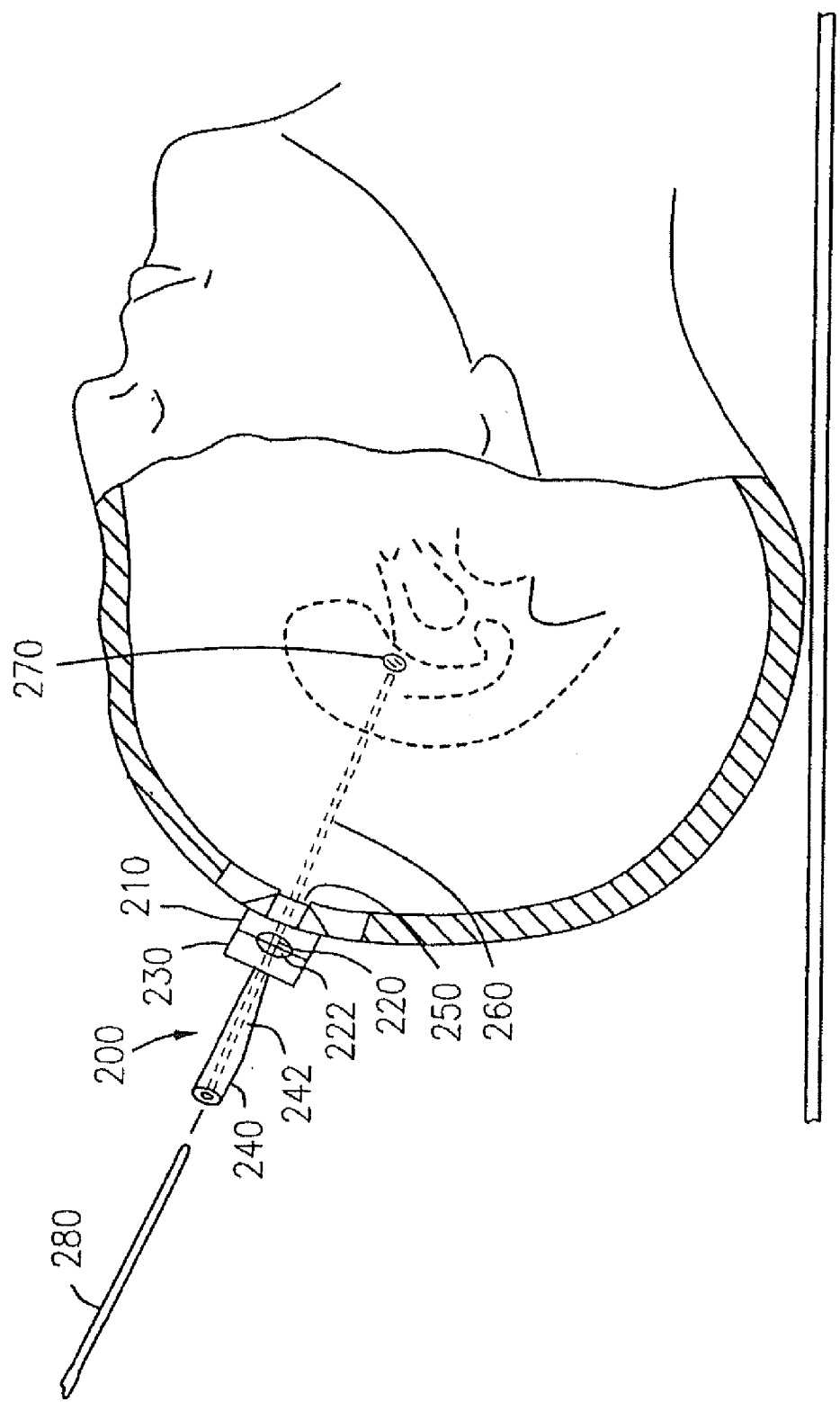
FIG. 2 is a side view of a patient on which the trajectory guide is being used.

Within some parts of a patient, it is critical to very accurately place a surgical instrument. For example, in neurosurgery, it is very critical to have instruments, such as catheters or needles, placed very accurately within the cranium or head of a patient. FIG. 2 shows a side view of a patient on which trajectory guide 200 is being used. The trajectory guide 200 includes a base unit 210, a movable member 220, a locking member 230 and a guide stem 240. The base unit 210 is attached to the skull of the patient. In the particular embodiment shown, the attachment is made by way of bone screws. However, it is contemplated, that there may be any number of ways to attach the base 210 to the skull. For example, the base 210 could also be threaded to screw into a burr hole 250. The flange could also be added to the base 210 to attach the base to the skull.

The movable member 220 has an axial opening 222 which is shown in FIG. 2 as dotted lines. The guide stem 240 also has an elongated opening 242 therein. The opening 242 is also shown as dotted lines in FIG. 2. The passage 242 in the guide stem 240 and the axial opening 222 in the movable member or ball 220 form a line or a trajectory 260 which intersects with a target 270 within the patient. The guide stem 240 and movable member or ball 220 form the first part of the trajectory 260. A surgical instrument or observational tool can be inserted into the opening 242 of the guide stem 240 and passed through the passage in the movable member 220 and then further inserted into the patient a selected distance to the target 270. The opening 242 in the guide stem 240 and the passage 222 in the movable member 220 guide a surgical instrument along the trajectory 260 to the target 270. Of course, the movable member 220 is locked into place by locking member 230 before a surgical instrument 280 is placed through the opening 242 in the guide member 240.

Figure 3:
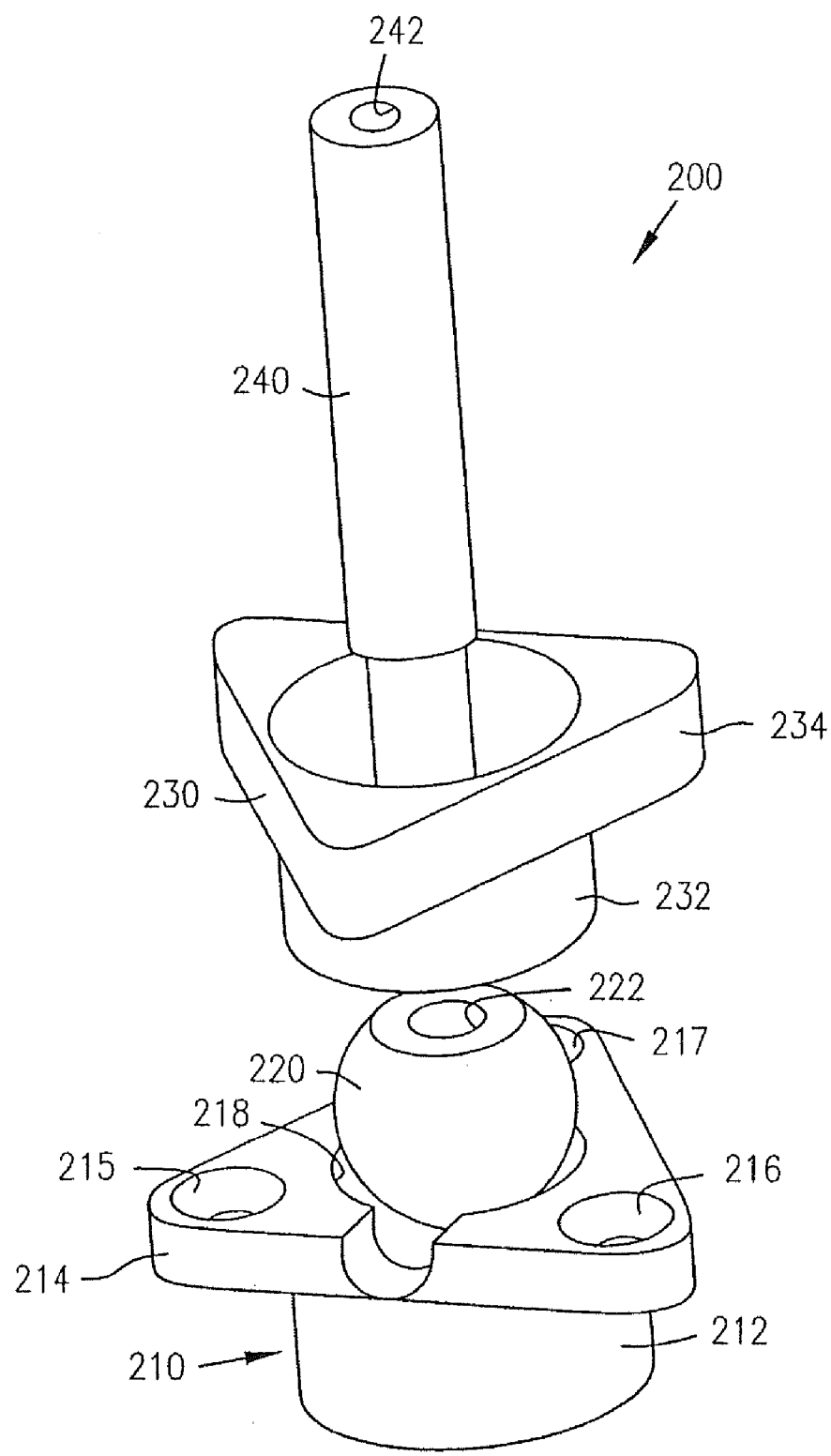
FIG. 3 is an exploded isometric view of the trajectory guide with a removably attached guide member installed.

FIG. 3 shows an exploded isometric view of the trajectory guide 200 with a guide member installed. As shown in FIG. 3, the trajectory guide 200 is comprised of a base 210, a movable member 220, a locking member 230, and a guide member 240. The base 210 includes a cylindrical portion 212 and a flange 214. The flange 214 includes a plurality of countersunk screw openings 215, 216, and 217. The countersunk screw openings 215, 216, and 217 receive bone screws which are screwed into the skull bone or the bone of a patient. The cylindrical portion 212 fits within the burr hole 250 in the patient. The base also includes a semi-spherical seat 218. Although not shown in FIG. 3, there is an opening in the base 210 having a first end which terminates at the seat 218 and another end which terminates at the bottom of the base 210.

As shown in FIG. 3, the movable member 220 is essentially a spherical member or a ball. The spherical member or ball fits within the seat 218. The spherical member or ball moves freely within the seat 218. The ball-shaped movable member 220 also has an opening. The opening passes through the ball shaped movable member. One end of the opening may have a set of internal threads therein, which can be used to receive mating threads which are placed onto the guide stem or member 240 or positioning stem (discussed with respect to FIG. 4).

The locking member 230 also has an opening therethrough. The locking member 230 includes a cylindrical bottom portion 232 and a flange 234. The opening through the locking member 230 has sufficient space to allow movement of movable member 220 when the locking member is in an unlocked or untightened position. Although not shown in FIG. 3 or 4, the bottom of the cylindrical portion 232 of the locking member 230 includes a set of external threads. The set of external threads engage a set of internal threads on the base unit 210 (shown in FIGS. 6a-6g). As will be detailed later, when the external threads of the locking member 230 are engaged with the threads on the base 210, a portion of the locking member engages the movable member 220 to fix the movable member and the axial opening 222 therethrough at a fixed position.

A guide stem or guide member 240 is also shown in FIG. 3. The guide stem has an elongated opening 242 therein. The elongated opening passes through the length of the guide stem 240. One end of the guide stem includes a set of external threads which engage the internal threads of the spherical, movable member 220. When the external threads of the guide stem 240 engage the internal threads of the movable member 220, the opening 242 is substantially aligned with the axial opening 222 in the movable member. The opening 242 and axial opening 222 form the first part or guide for the trajectory 260 to the target 270 within the patient. It should be noted that the movable member 220 need not necessarily be a spherical element, although the spherical shape allows the ball to have a universal joint type swivel action which is preferred. It should also be noted that the locking member 230 can be formed in most any shape. A flange 234 is useful in that it allows additional leverage for tightening or loosening the locking member. Any shape capable of being turned or placed into a locking position with respect to the movable member 220 is acceptable.

Positioning Member Example

Figure 4:
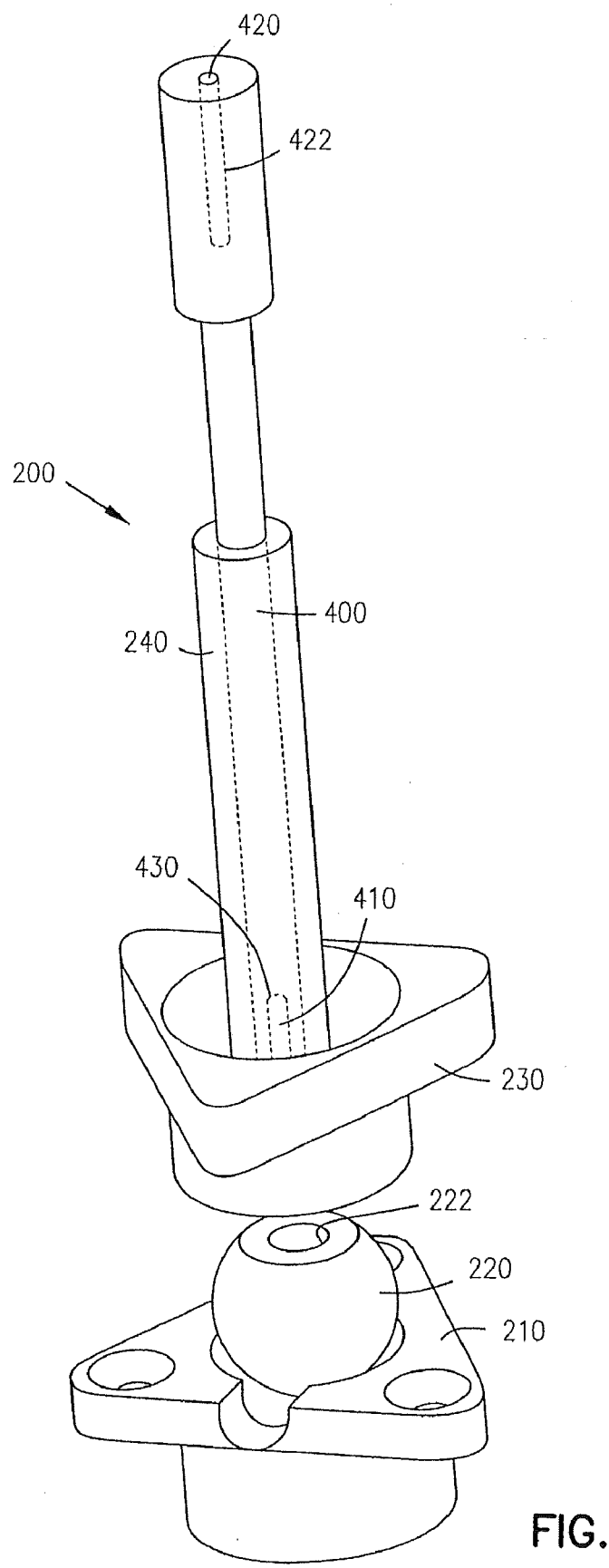
FIG. 4 is an exploded isometric schematic view of the trajectory guide with a removably attached positioning member installed inside the removably attached guide member.

FIG. 4 is a schematic illustration that shows an exploded isometric schematic view of the trajectory guide 200 with a positioning member 400. FIG. 4 is a schematic illustration intended to illustrate the functionality of the positioning member. In FIG. 4, an end 410 of positioning stem 400 has been inserted into guide stem or guide member 240. Positioning stem 400 may also include a first locator 420 and second locator 430. First locator 420 includes a small opening 422 located at one end of the positioning stem 400. The small opening 422, which is shown in phantom in FIG. 4, is filled with a fluid or a substance that can be seen by a scanning device such as the MRI scanning device 100 described and shown in FIG. 1. After a fluid or substance is inserted into the opening 422 the end is sealed with a cap and adhesive. Similarly, the second locator 430 includes an opening 432 which contains a substance which is readable by a scanner such as an MRI scanner shown in FIG. 1. As shown in FIG. 4, the first locator 420 and the second locator 430 are coaxial with the axis of the cylinder formed by the positioning stem 400. It is contemplated that a first locator 420 and a second locator 430 could also be formed in an offset position from the axis of the cylinder formed by the positioning stem 400.

Figure 10A:
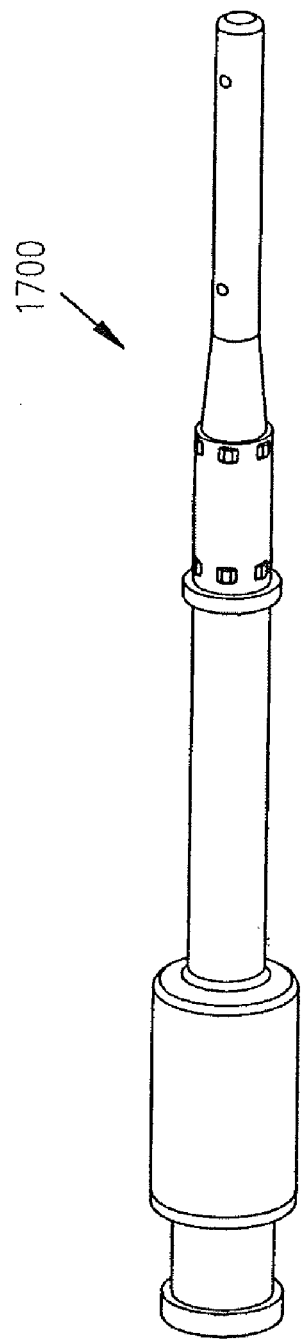
FIG. 10a is an isometric view of a preferred embodiment of a alignment or positioning member for the trajectory guide.
Figure 10B:
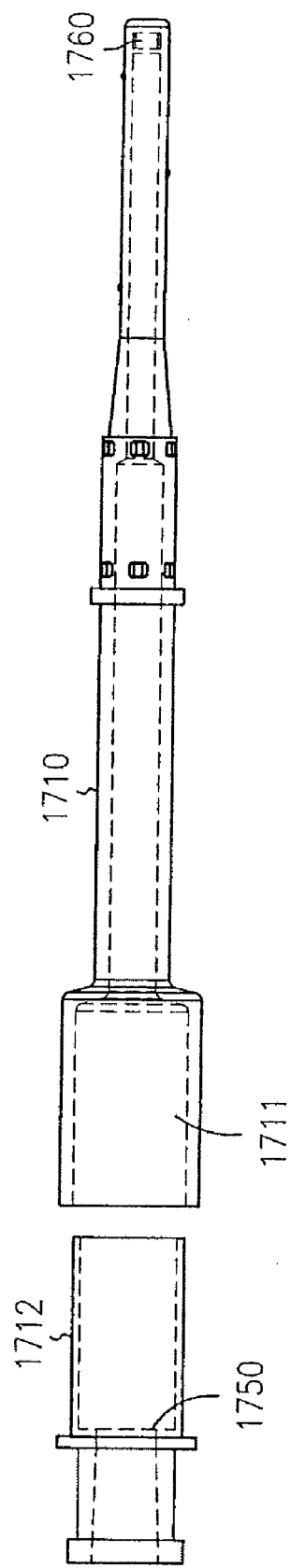
Figure 10C:
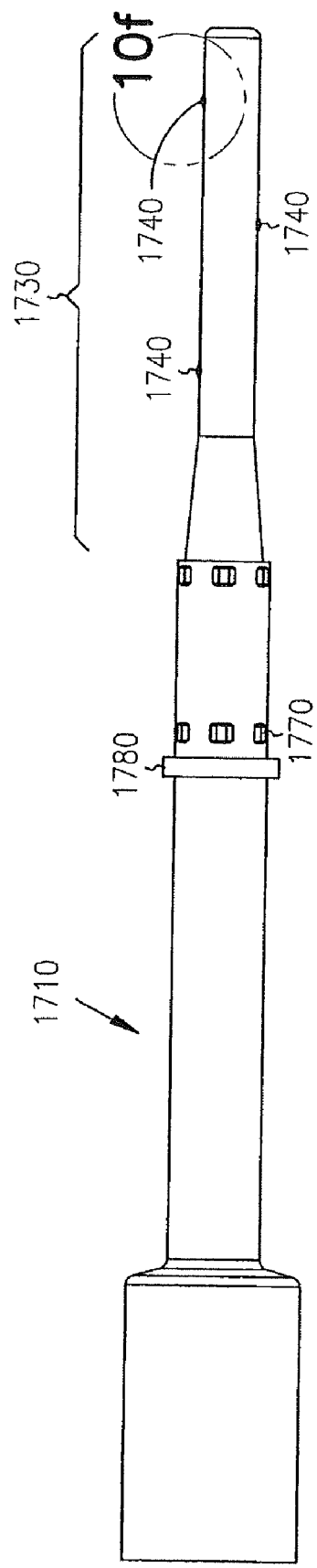
FIG. 10c is a side view of a portion of the embodiment of FIG. 10b.
Figure 10D:
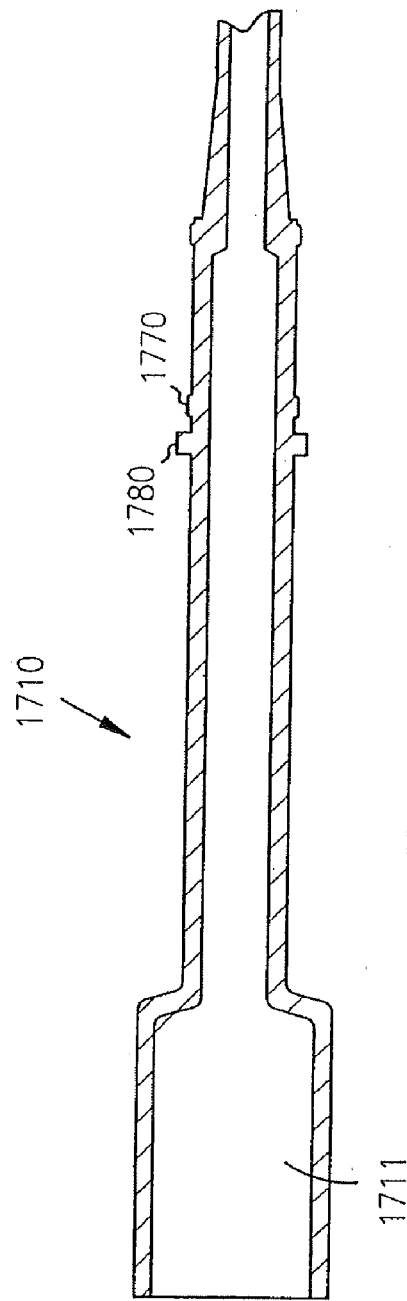
FIG. 10d is a side cross sectional view of the embodiment of FIG. 10c.
Figure 10E:
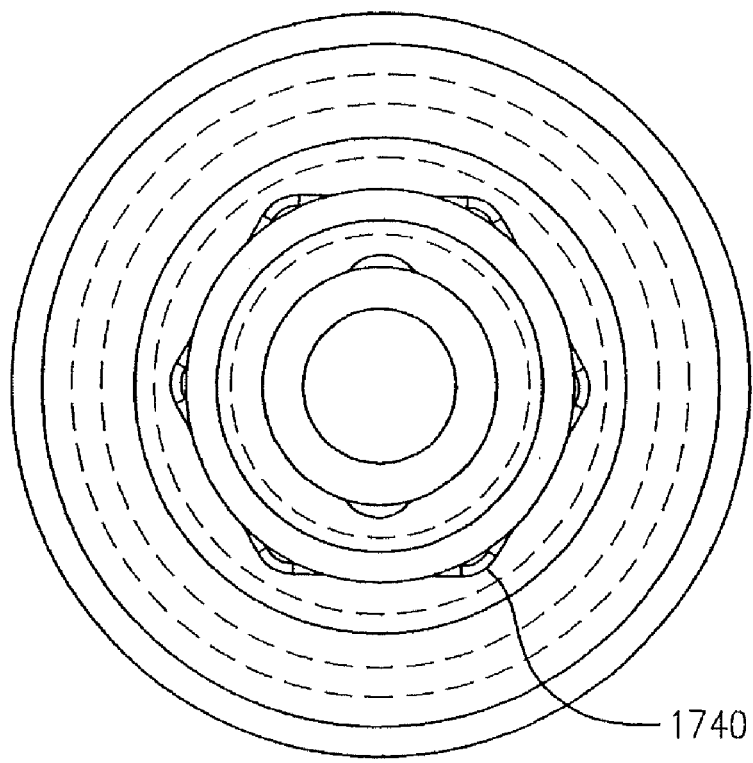
FIG. 10e is an end view of the embodiment of FIG. 10d.
Figure 10F:
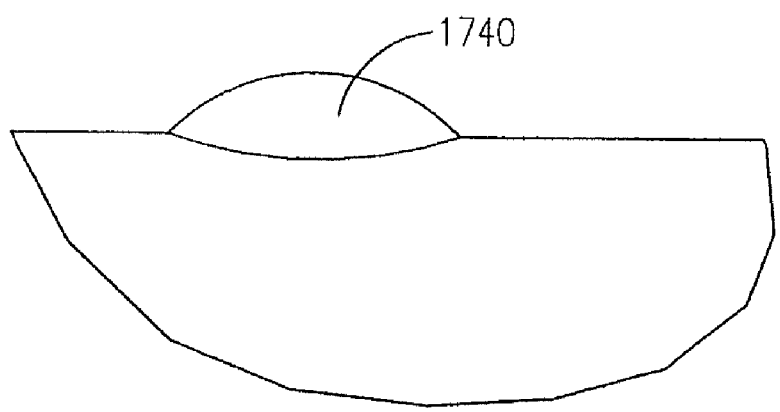
FIG. 10f is a detailed view of a portion of the embodiment of FIG. 10e.

FIGS. 10a-10f show one example of a positioning stem. In FIG. 10b, positioning stem 1700 includes a main portion 1710 having a substantially hollow portion 1711 capable of accepting optional end cap 1712. This two-piece construction may be used, for manufacturing reasons, but is not required if a one-piece construction performing the same functionality is desired. A fluid such as (but not necessarily) saline, which is readable by nuclear magnetic resonance (NMR) imaging system, is housed or kept in a chamber 1711 of positioning stem 1700. In this example, the fluid is contained between a proximal portion 1750 of end cap 1712 and a distal portion 1760 of main portion 1710. The fluid within chamber 1711 can be easily located under NMR and is used for alignment of the positioning stem, so that opening 222 within movable member 220 is on a straight line trajectory with a target within the patient.

Alternatively, positioning stem 1700 may include a region of solid material that appears on the MR image only by virtue of its absence of MR visibility.

A series of bump-like protrusions or other features 1740 are arranged around a circumference of a distal portion of tapered distal shaft end 1730. Similarly, a series of box-like features 1770 are arranged around the central portion of the main portion 1710, proximal of the tapered distal shaft end 1730 and distal of a stop 1780. Features 1740 and 1770 are optional features that help hold positioning stem 1700 in place as it is inserted into guide stem 240 until it is stopped in place by stop 1780.

Movable Member Example

Figure 5A:
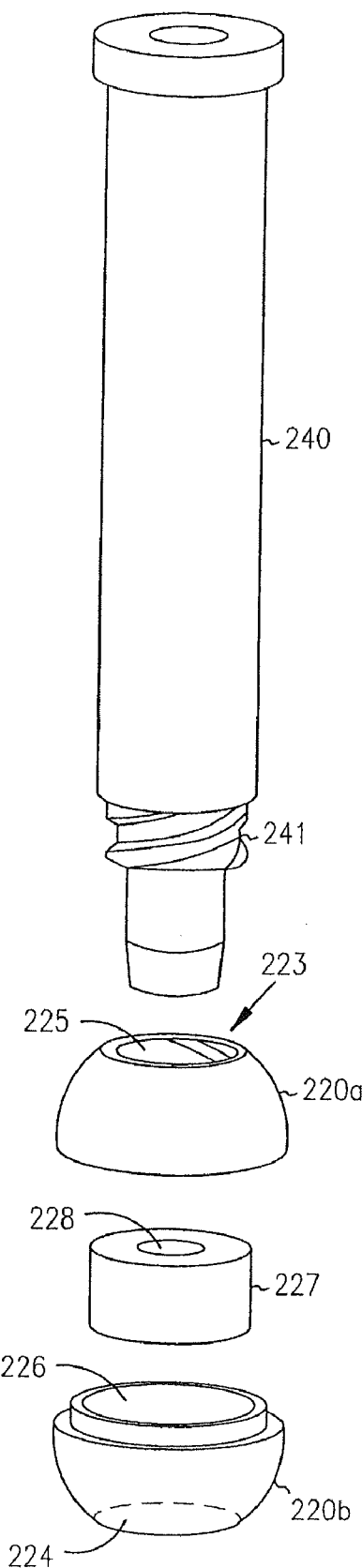
FIG. 5a is an exploded isometric view of the movable member or ball and guide stem of the trajectory guide.
Figure 5B:
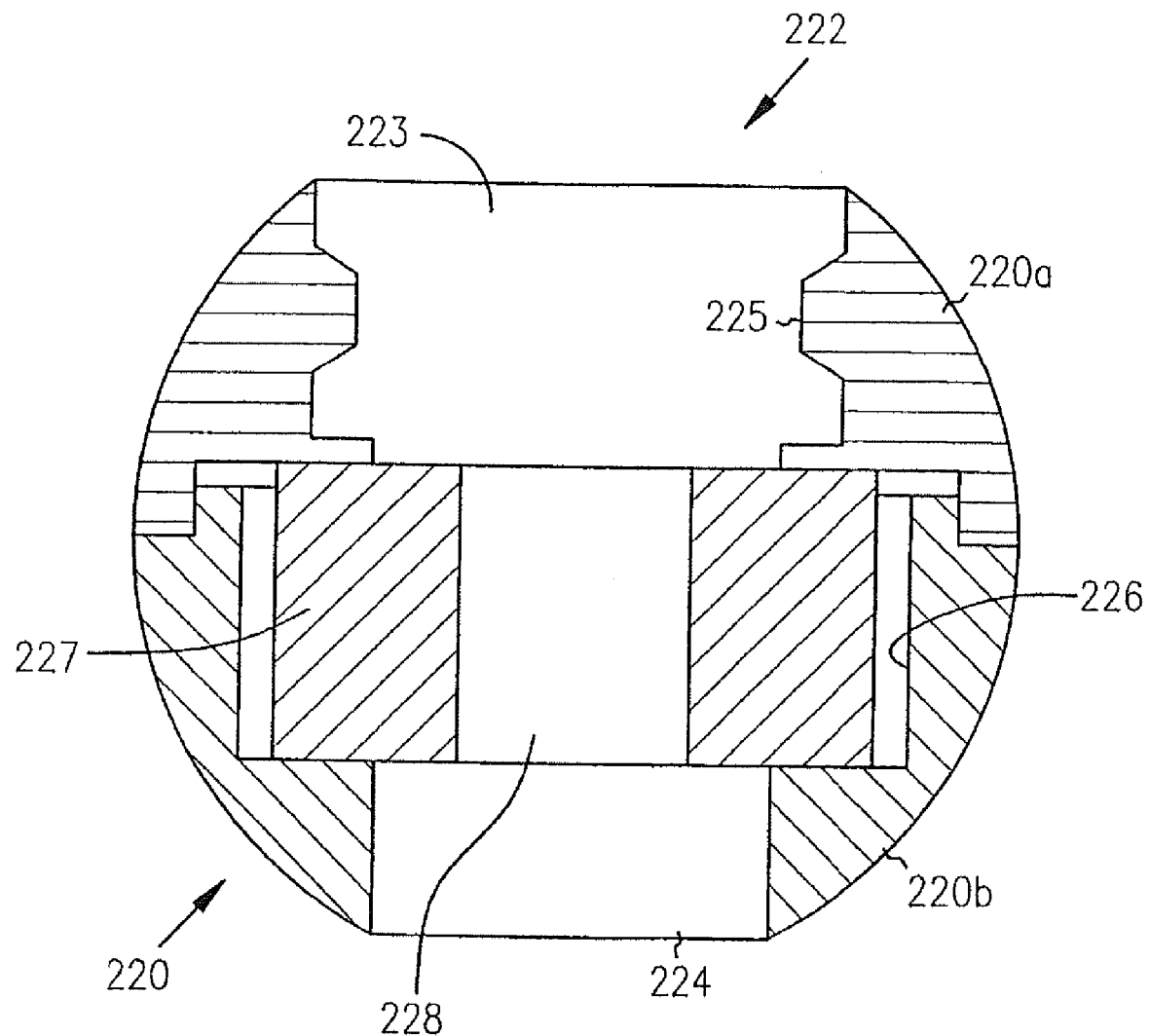
FIG. 5b is a cross-sectional view of the movable member or ball of the trajectory guide.

FIGS. 5a and 5b show one example of a movable member 220 that includes two mating, substantially hemispherical portions 220a and 220b that, when assembled, provide a substantially spherically shaped movable member 220. Movable member 220 has an axial opening 222 therein. Axial opening 222 includes a first opening 223 in upper hemispherical portion 220a, and a second opening 224 in lower hemispherical portion 220b. The inside surface of first opening 223 is threaded as indicated by reference numeral 225. First opening 223 and threads 225 receive an external threaded portion 241 of guide stem 240. Second opening 224 is of a sufficient diameter to allow an instrument, such as a needle, probe, catheter, endoscope, or electrode to pass through the axial opening 222. Movable member 220 is made of a rigid or semi-rigid biocompatible polymer material. Suitable materials include polycarbonate or DELRIN®.

Lower hemispherical portion 220b further includes a recess 226 sized and shaped to accept a relaxable stabilizer 227. Relaxable stabilizer 227 is sized and shaped to complement the size and shape of recess 226, thus fitting closely inside recess 226 so as not to move out of proper position inadvertently. Also, relaxable stabilizer 227 has an axial opening 228 that generally is coaxial with axial opening 222 of the movable member 220.

Because movable member 220 is preferably a relatively stiff material such as polycarbonate, and relaxable stabilizer 227 is relaxable and therefore made of a relatively more compliant material such as silicone, the two hemispherical portions 220a and 220b and the relaxable stabilizer 227 will generally be manufactured separately and assembled into the configuration shown in FIG. 5b. However, the scope of the invention includes an integrally constructed movable member having a material that is relaxable, and that otherwise performs the functions of the relaxable stabilizer as described below. Other suitable materials for relaxable stabilizer 227 include latex, C-flex, Viton, Buna-N, polyurethane, Kraton, and Santoprene.

FIGS. 5c through 5g illustrate one process of positioning a instrument 229 within the movable member 220 so as to restrict or prohibit axial motion of the instrument 229.

Figure 5C:
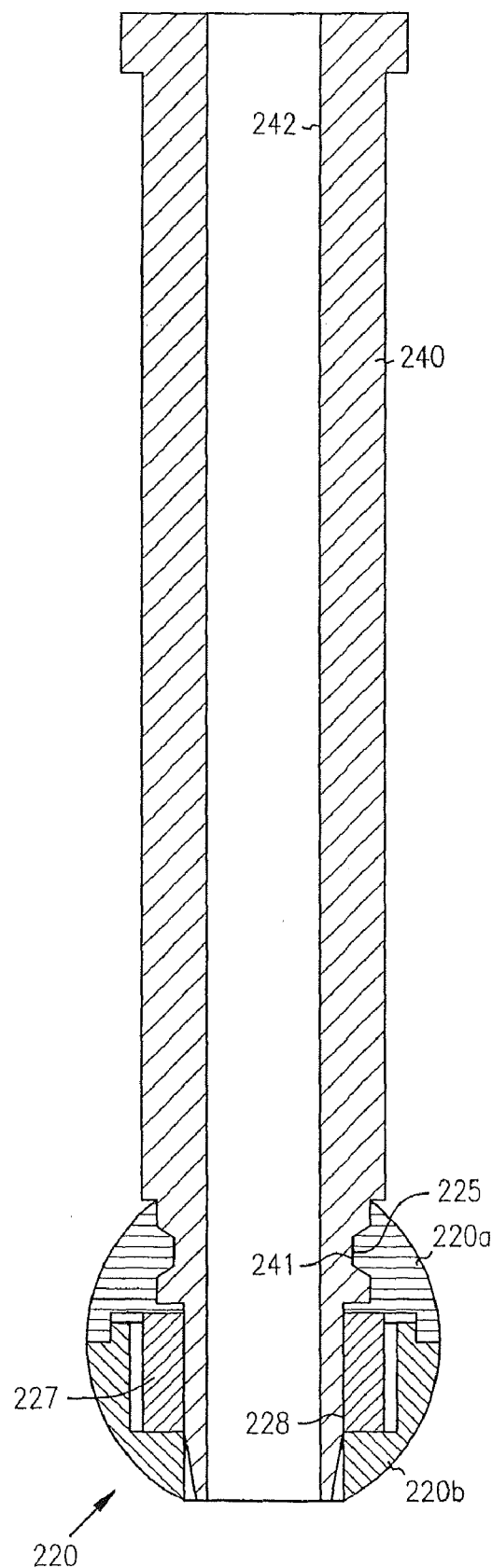
FIG. 5c is a cross-sectional view of the movable member or ball of the trajectory guide after insertion of the relaxable stabilizer and removably attached guide member.

Before attachment of guide stem 240 to movable member 220 as shown in FIG. 5c, a suitable tool (not shown) is used to stretch (or otherwise increase the inside diameter of) the relaxable stabilizer 227, until the axial opening 228 of relaxable stabilizer 227 is large enough to accept the outer diameter of the guide stem 240. This permits the stem to be fully inserted into the movable member 220, through the stretched axial opening 228 in relaxable stabilizer 227, and then screwed into place utilizing external threads 241 and internal threads 225. The result of this operation is shown in FIG. 5c.

Relaxable stabilizer 227 is sized and shaped such that: (1) upon removal of the tool, the previously stretched inside diameter of its axial opening 228 will attempt to return to a size somewhat less than the outer diameter of guide stem 240; but (2) relaxable stabilizer 227 will not hold guide stem 240 so tightly that it cannot be removed by unscrewing it from the movable member 220.

Figure 5D:
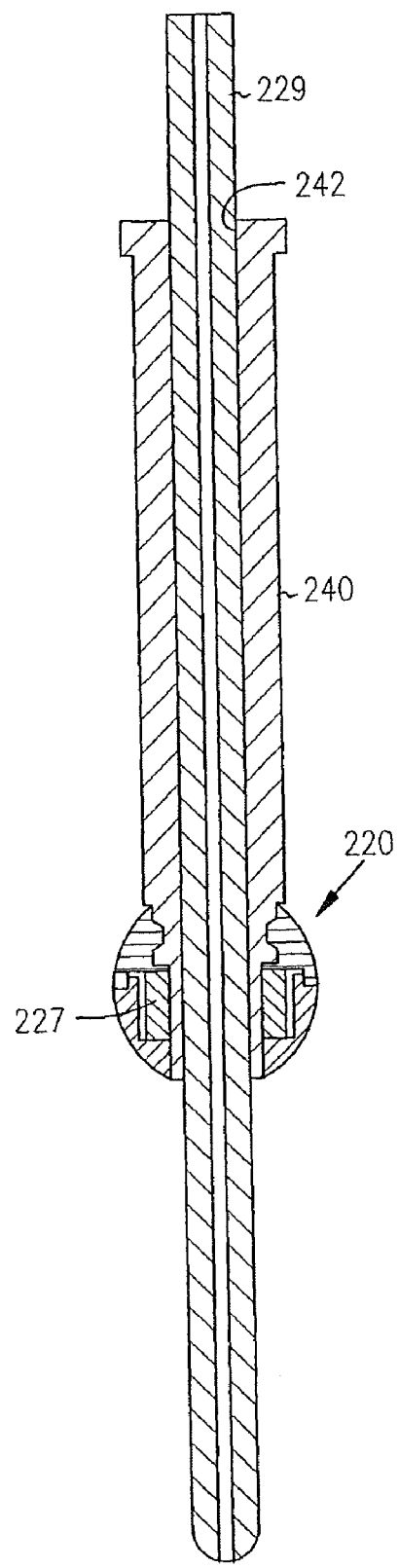
FIG. 5d is a cross-sectional view of the assembly of FIG. 5c, after further insertion of a catheter or instrument.
Figure 5E:
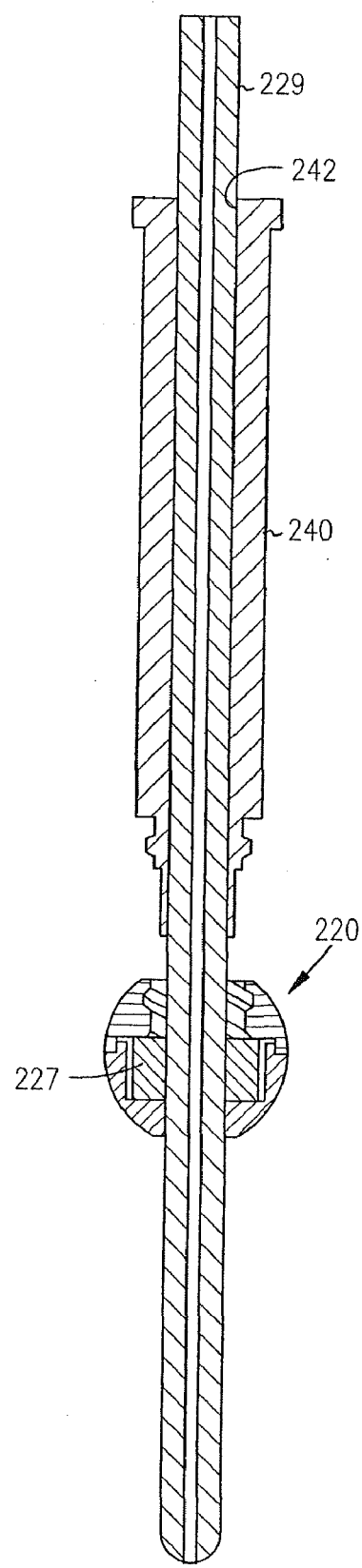
FIG. 5e is a view of the assembly of FIG. 5d, after unscrewing and partial removal of the removably attached guide member.
Figure 5F:
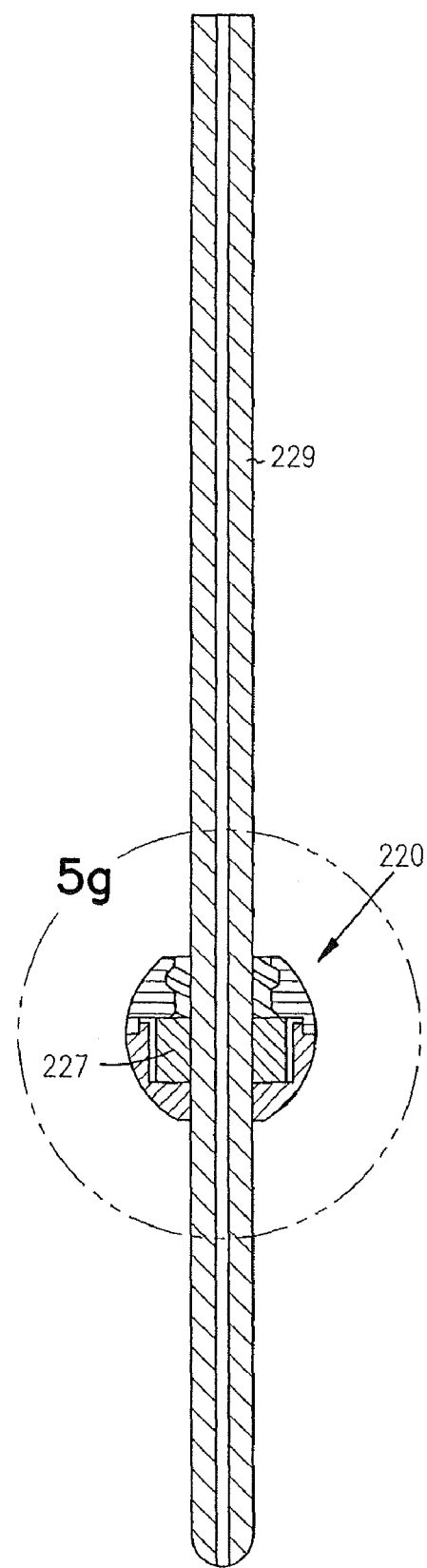
FIG. 5f is a view of the assembly of FIG. 5e, after complete removal of the removably attached guide member.
Figure 5G:
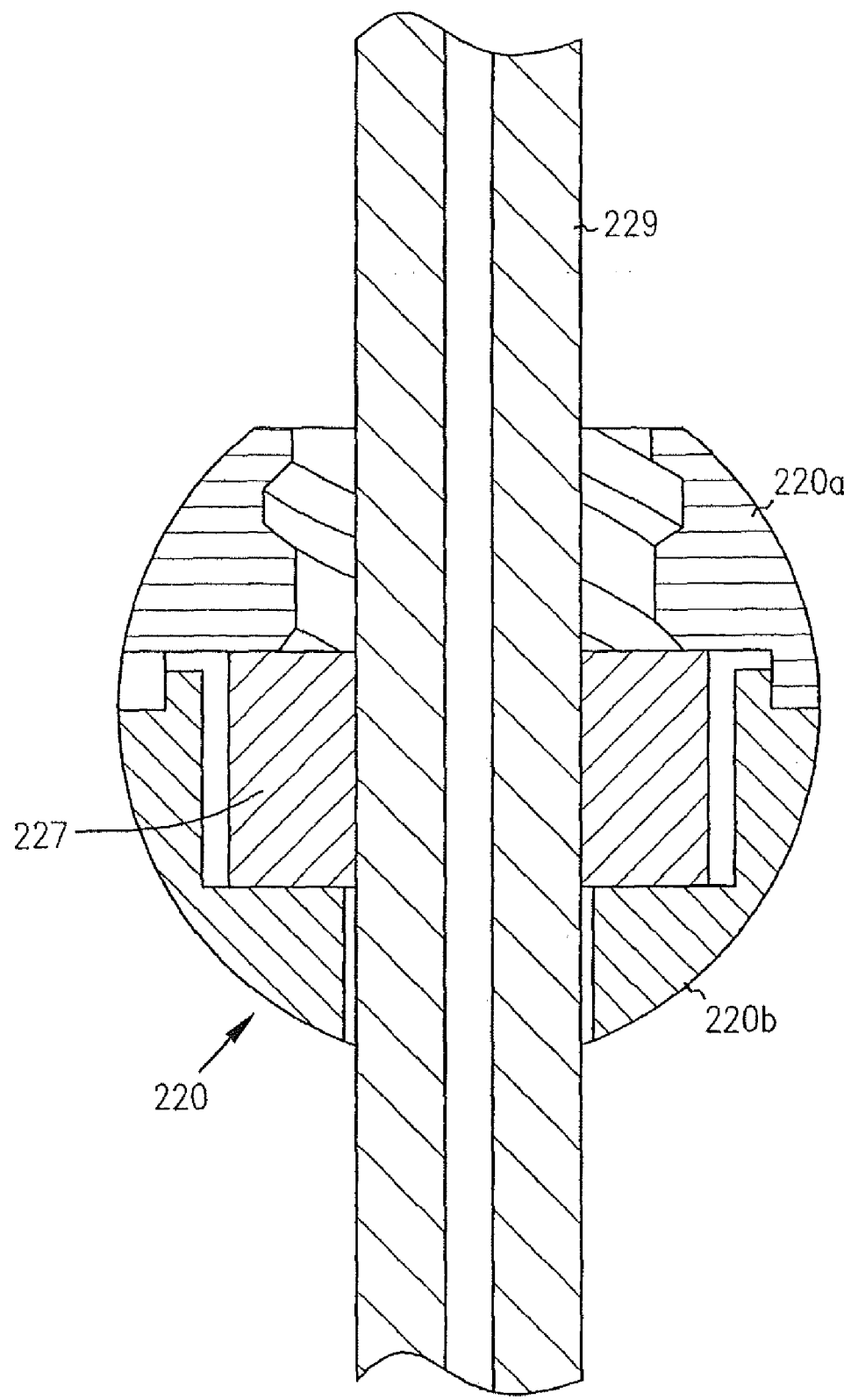
FIG. 5g is a close up side view of a portion of FIG. 5f.
Figure 6A:
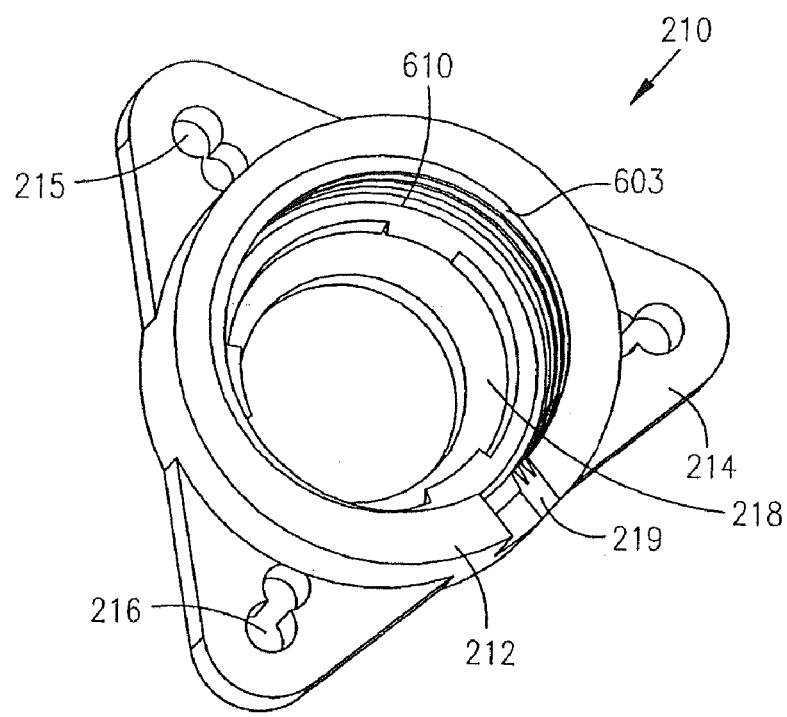
FIGS. 6a and 6b are isometric views of one example of a base of the trajectory guide.
Figure 6B:
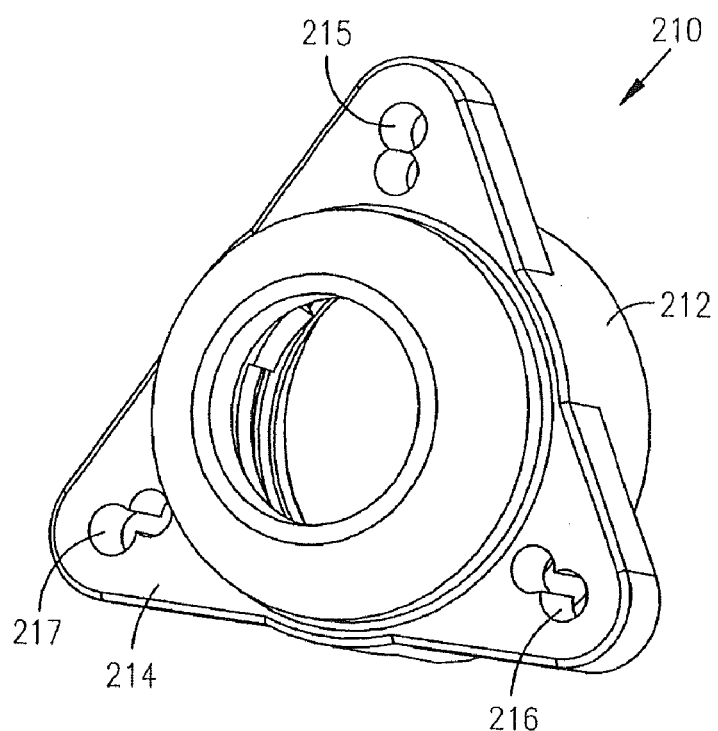
Figure 6C:
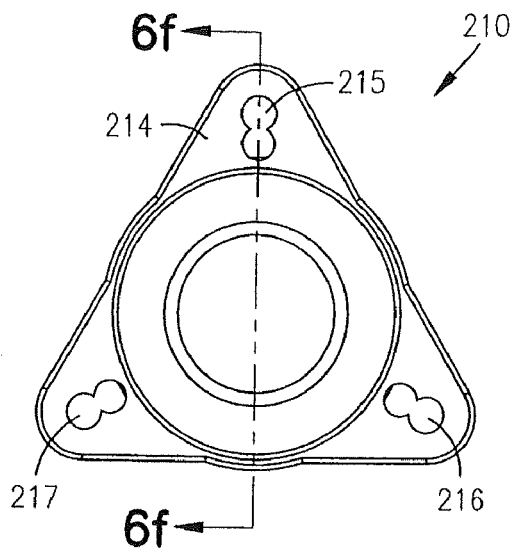
FIGS. 6c-6e are bottom, side, and top views, respectively, of the base of FIGS. 6a and 6b.
Figure 6D:
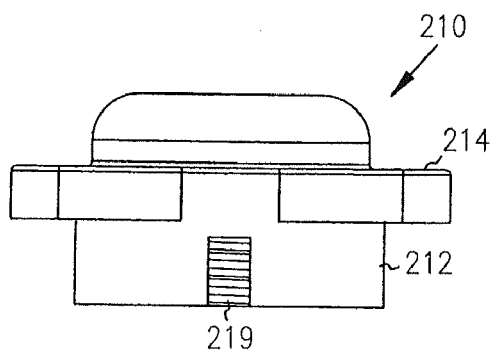
Figure 6E:
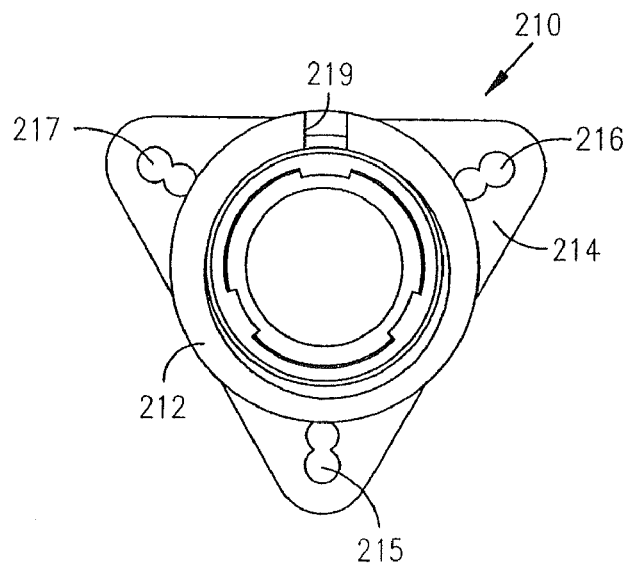
Figure 6F:
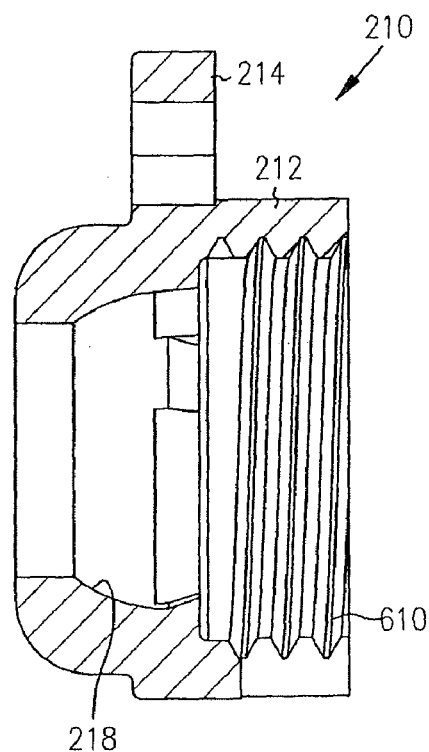
FIG. 6f is a cross sectional view taken along the line 6f-6f of FIG. 6c.
Figure 6G:
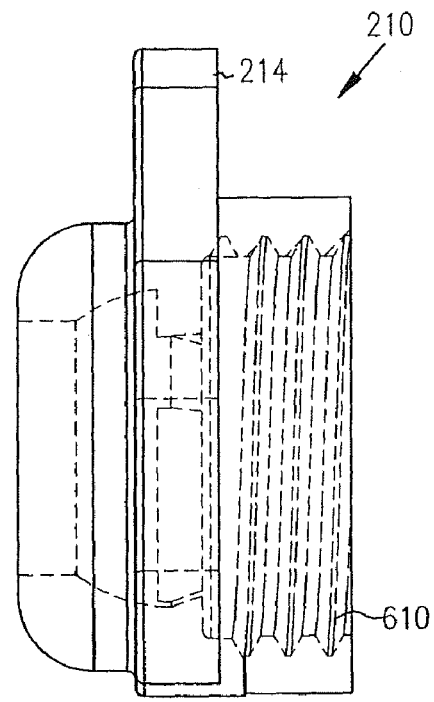
FIG. 6g is a side view of the base of FIG. 6c.
Figure 7A:
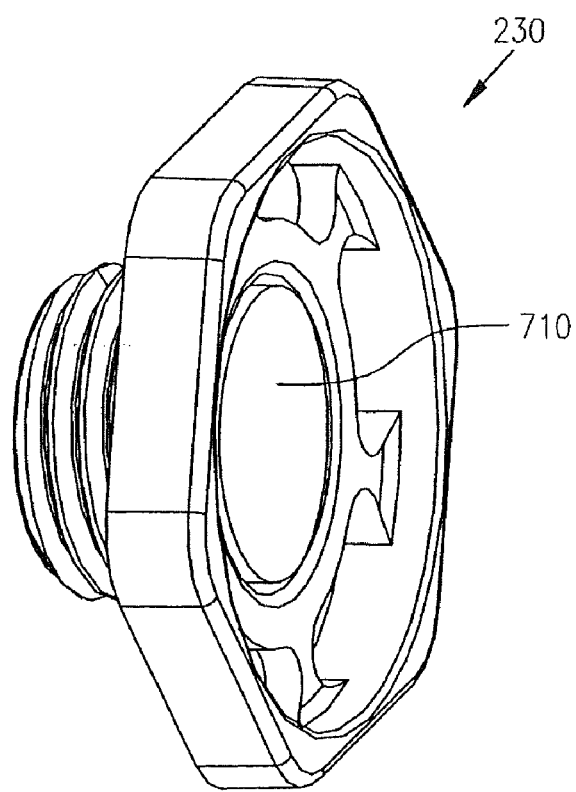
FIGS. 7a and 7b are isometric views of one example of the locking member of the trajectory guide.
Figure 7B:
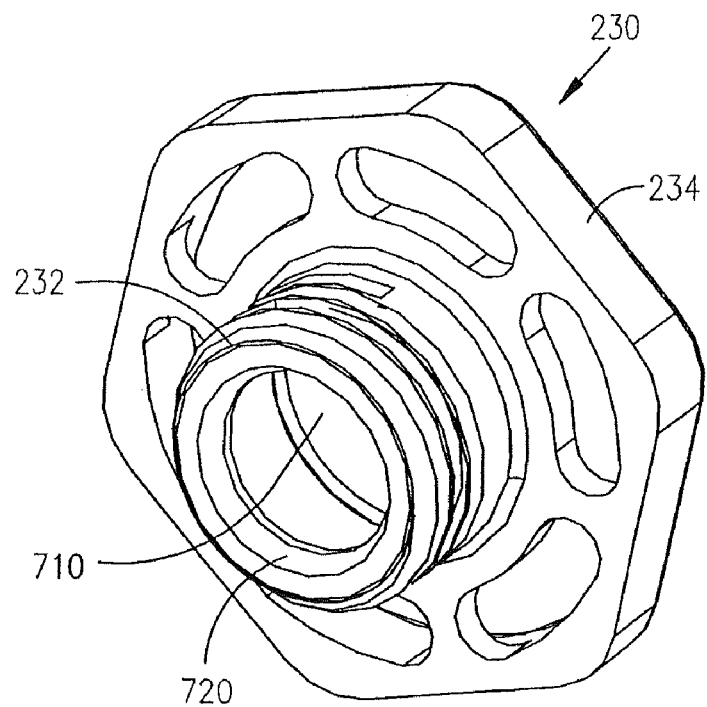
Figure 7C:
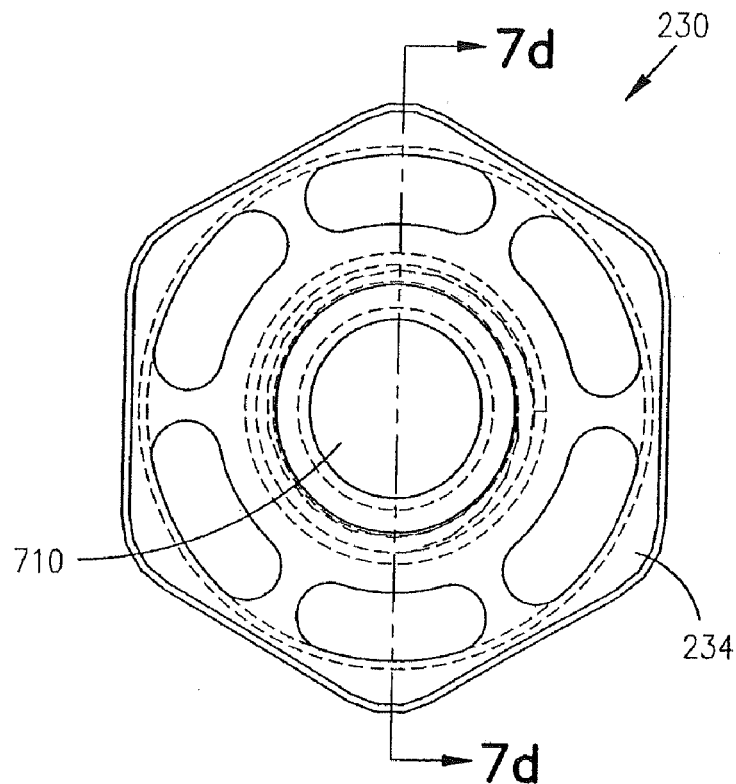
FIG. 7c is a top view of the example of the locking member of the trajectory guide.
Figure 7D:
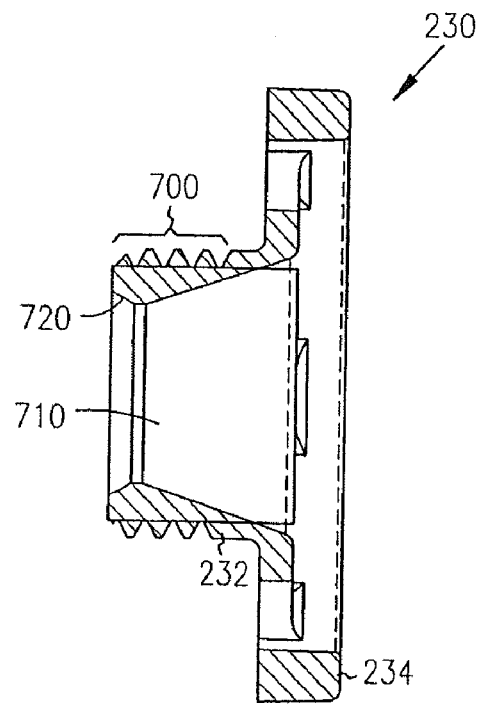
FIG. 7d is a cross-sectional view of the example of the locking member of the trajectory guide, taken along the line 7d-7d of FIG. 7c.

Before removal of guide stem 240, an instrument 229 may be inserted into the passage through opening 242 of guide stem 240, as shown in FIG. 5d. Then, as guide stem 240 is removed from the vicinity of relaxable stabilizer 227 as shown in FIG. 5e, relaxable stabilizer 227 will continue to return to a size that applies sufficient pressure or friction to the outer diameter of the instrument 229. This prevents axial migration of instrument 229, both while removing the guide stem 240 entirely over the proximal end of instrument 229, and also during any subsequent movement of the proximal segment of the instrument 229 as instrument 229 is secured or tunneled as described herein. FIGS. 5f and 5g are closeup views of relaxable stabilizer 227 after it is relaxed back into a position that will securely hold instrument 229 in place.

From this description it can be appreciated that the relaxable stabilizer 227 operates in a manner exactly opposite from known stabilization techniques, because the relaxable stabilizer 227 relies on self-relaxation to provide stabilizing force to instrument 229, as opposed to techniques in which compression of a material provides stabilization. For example, the well-known Touhy-Borst valve uses a compressible "O-ring" to provide stabilization of objects such as guidewires, leads, catheters, and the like upon twisting by a clinician's hand, but the present relaxable stabilizer stabilizes instruments by relying on relaxation, not compression.

Base Example

FIGS. 6a to 6g show an example of base 210 of trajectory guide 200. Base 210 includes a generally cylindrical portion 212 and a flange 214. Flange 214 includes openings 215, 216, and 217. Flange 214 also a seat 218 that receives movable member 220. Seat 218 is part of an opening 600 which includes an internally threaded portion 610. Internally threaded portion 610 is dimensioned so as to receive the threads of cylindrical portion 232 of locking member 230. Groove 219 lies in base 210 and is sized and shaped to accommodate a flexible instrument 229 or other instrument, as discussed further herein with respect to a stabilization or tunneling procedure.

In other embodiments, base 210 may separated into two or more pieces. FIGS. 13a-13e, 14a-14b, 15a-15b, 16a-16c, 17, and 18a-18c show several examples of structures and methods of using a multi-piece base 210, such as a separate seat/mount and an internally threaded locking collar attachable thereto The internal threads of the locking collar receive the external threads of the cylindrical portion 232 of locking member 230. By separating base 210 into more than one piece, its profile above the skull may advantageously be reduced.

Lockable Member Example

FIGS. 7a-7d illustrate an example locking member 230 of trajectory guide 200. Locking member 230 includes cylindrical portion 232 and flange 234. The external surface of the cylindrical portion 232 is threaded to form a threaded external surface 700. The threads associated with the externally threaded surface 700 are dimensioned so as to engage the internally threaded surface 610 of opening 600 of base 210. Locking member 230 also includes an opening 710 which passes through locking member 230. Locking member 230 also has a locking surface 720. In this particular example, locking surface 720 is shaped so that it smoothly engages the spherical face of movable member 220. Flanges 234 are outwardly extended so that the threads of the threaded surface 700 can be easily engaged with internal threads 610 of opening 600 of base 210. Other geometric shapes could be used for the locking member and other locking surfaces could be employed.

Instrument Placement Example

In operation, a patient undergoes a scan with an apparatus such as an MRI or magnetic resonance imaging system 100 as part of a normal diagnostic medical procedure. A scan can be used to locate a particular organ within a patient or to locate lesions or any other target 270 within the patient. It should be noted that targets are not necessarily limited to being within the head of a patient. There can also be other areas of a patient where it would be critical to accurately place a surgical or observational tool. In addition, it should also be noted that the patient need not necessarily be human. A patient may include any living animal. Once a target is found and located using an MRI or other scanning system, base 210 of trajectory guide 200 can be attached to the patient. The base is affixed to the patient in an area near the target 270. The computer 102 of scanning device 100 is used to determine the exact location of the target 270. The exact location can be found in any type of coordinate system, although normally a Cartesian coordinate system is used. Once base 210 is attached to the patient, the remaining portions of trajectory guide 200 are attached to base 210. In other words, movable member 220, guide stem 240, locking member 230, and positioning stem 400 are added to form a complete trajectory guide 200.

Scanning system 100 reads first locator 420 and second locator 430 of positioning stem 400. A line defined by first locator 420 and second locator 430 is calculated by computer 102. The calculated line corresponds to the center line of axial opening 222 and opening 242 of guide stem 240. If the line aligns with target 270, locking member 230 is used to lock movable member 220 into position. If the line does not intersect target 270, positioning stem 400 is moved until the line formed by first locator 420 and second locator 430 intersects target 270. If the patient and positioning stem 400 can be easily reached by a surgeon during a scanning operation, positioning stem 400 can be moved or readjusted manually. If the patient is remote from the surgeon or cannot be reached by the surgeon, a hydraulic or other actuator may be used to move positioning stem 400. Once such a trajectory line is formed, the locking member 230 is secured.

After fixing the position of movable member 220, positioning stem 400 is removed from guide stem 240. Opening 242 in guide stem 240, and opening 224 in movable member 220 form the trajectory 260. An instrument 229 may be placed through the guide opening to intersect target 270.

Tunneling Procedure Example

Figure 8A:
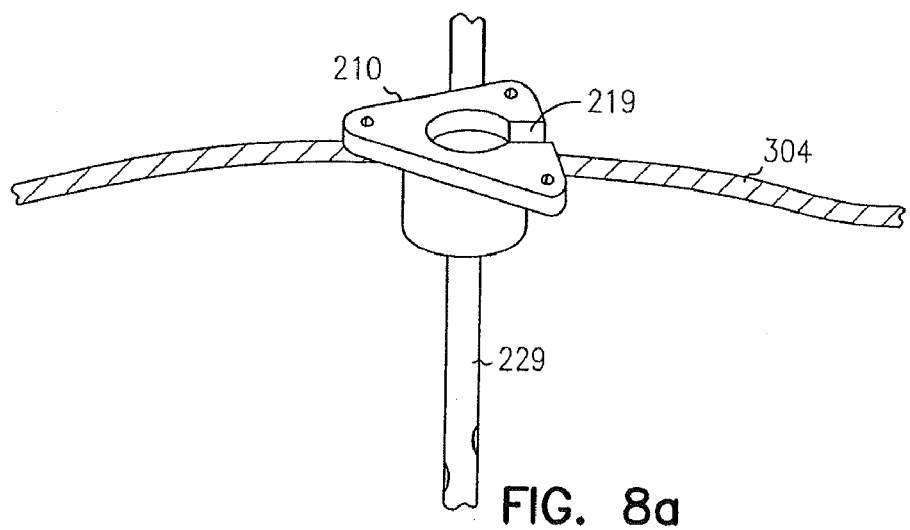
FIGS. 8a, 8b and 8c are perspective views showing the use of a base with a flexible instrument that is tunneled under a skin flap.
Figure 8B:
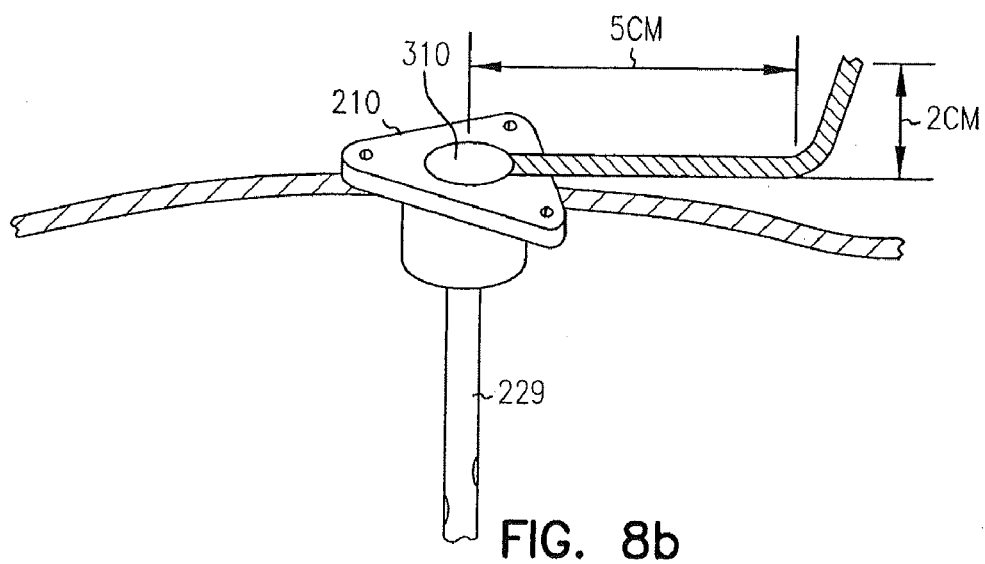
Figure 8C:
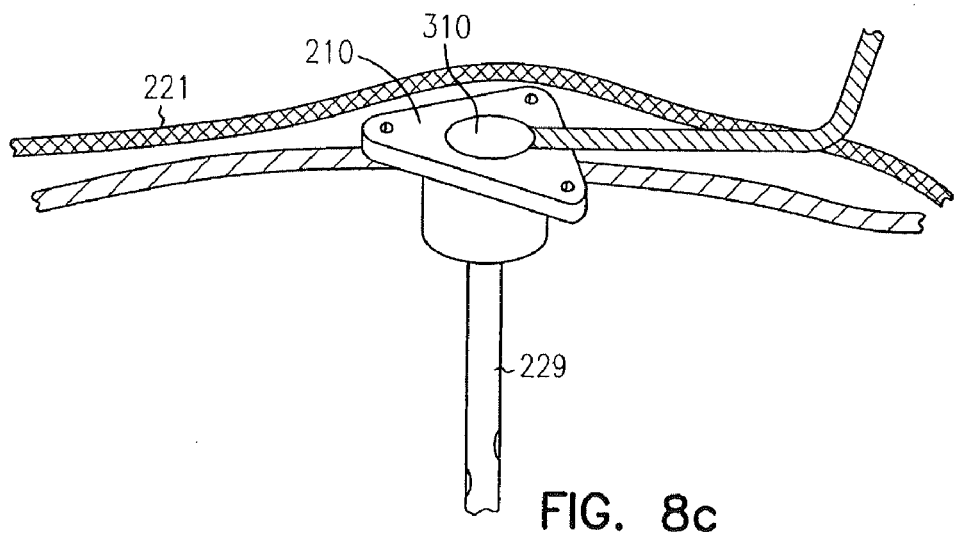
Figure 9A:
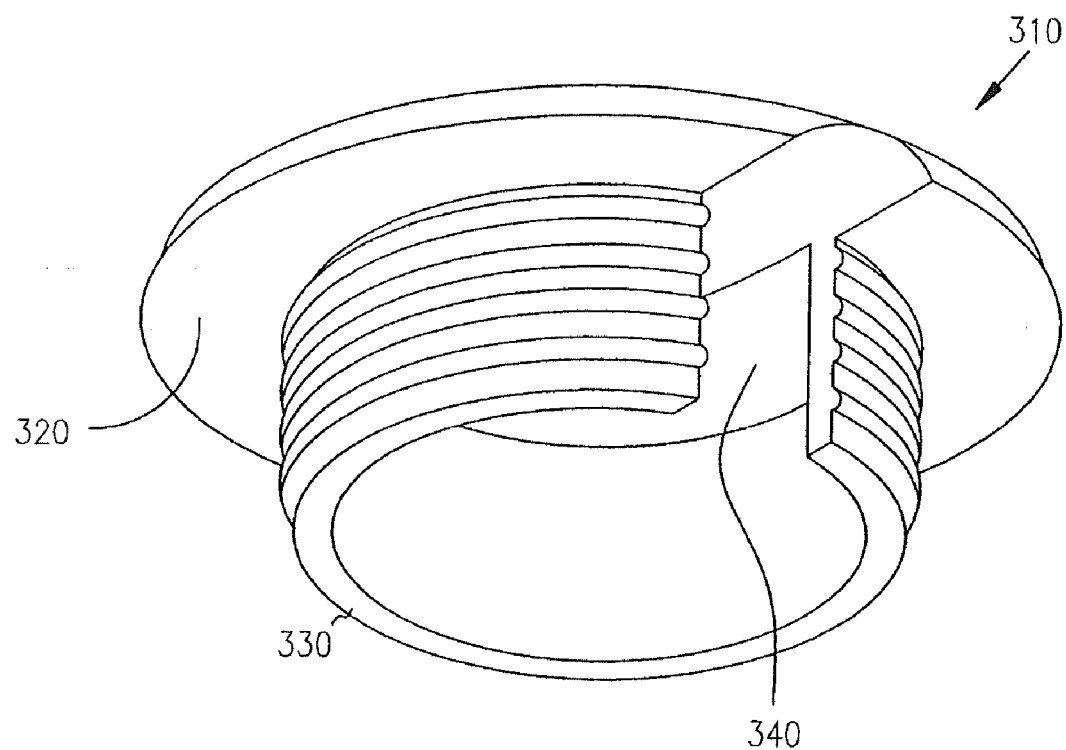
FIG. 9a is a perspective view of one example of a cap member of a trajectory guide.
Figure 9B:
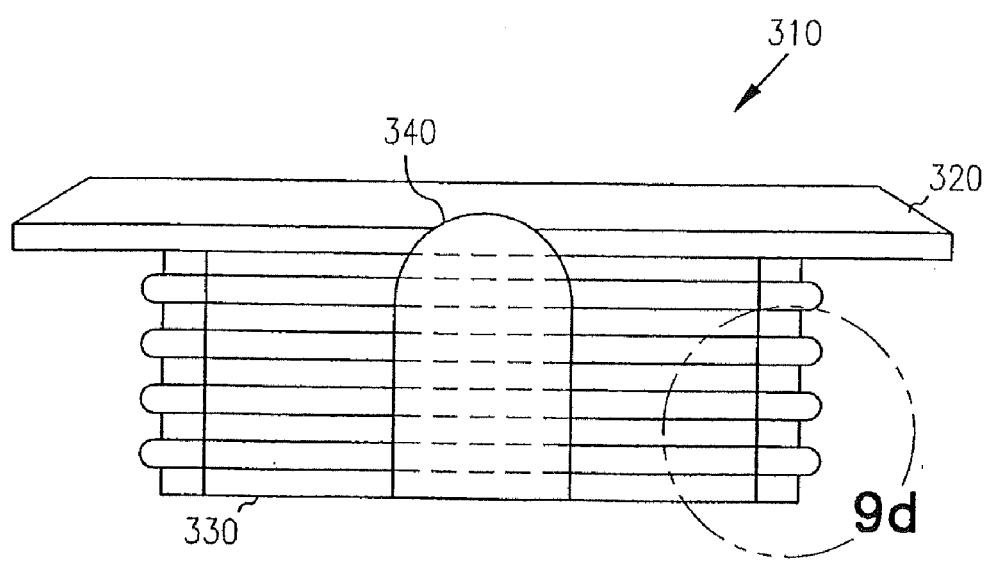
Figure 9C:
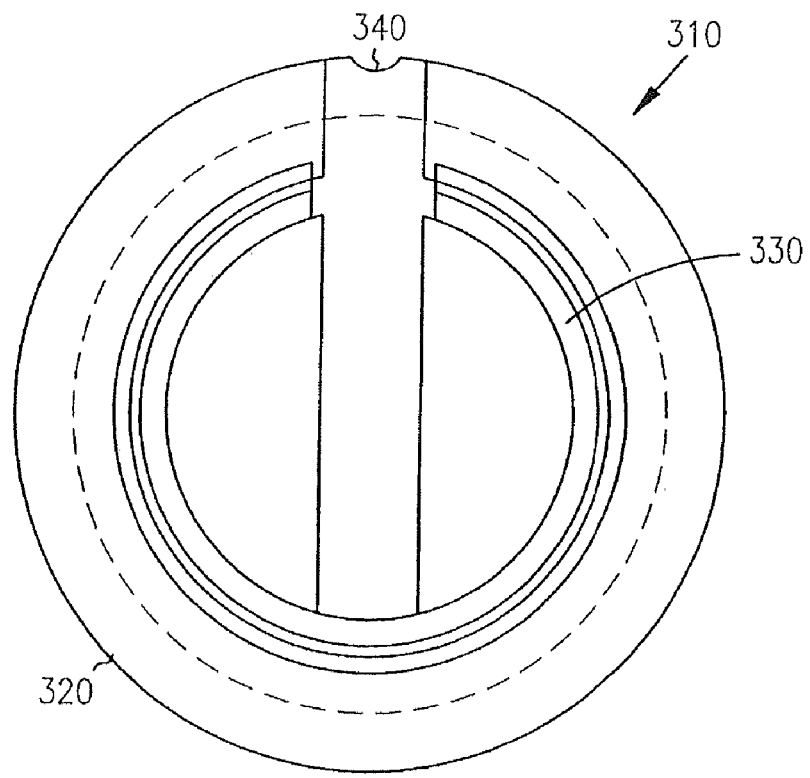
Figure 9D:
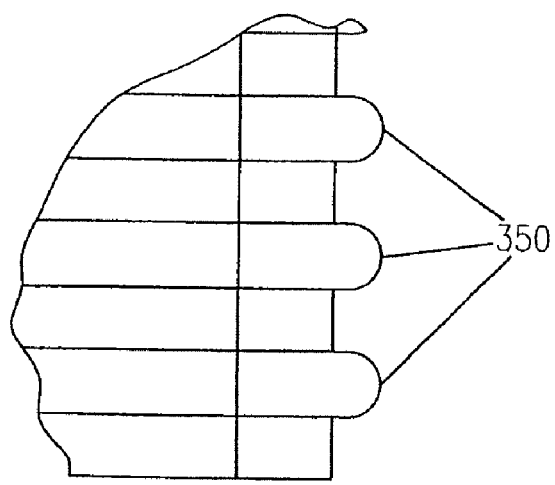
FIG. 9d is a close up side view of a portion of FIG. 9b.

FIGS. 8a, 8b and 8c illustrate one procedure for securing the distal portion of a flexible instrument 229 so that the proximal portion of flexible instrument 229 may be tunneled under a skin flap. FIG. 8a shows base 210 positioned against a surface 304 of a body, e.g., a skull of a patient.

Base 210 is attached to the patient as described above. Flexible instrument 229 extends through movable member 220 to target location 270 and is secured in place by relaxable stabilizer 227 (not shown in FIGS. 8a 8c), again as described above. As shown, guide stem 240 has been removed over the proximal (as shown, the upper) portion of flexible instrument 229. In this example, base 210 is a multi-piece base in which the locking collar has also been removed.

In FIG. 8b, the proximal portion of flexible instrument 229 has been laterally bent into groove 219 (shown in FIG. 8a and covered by the instrument 229 in FIG. 8b) so that it lies generally parallel to the surface 304 of the body and extends for approximately 5 cm. As noted before, this distance is a typical example, but depends on the clinical situation. The proximal end of instrument 229 is then turned generally upward, away from the surface 304 of the body, for a distance of approximately 2 cm (again, a typical example but dependent upon clinical conditions). A rigid or flexible cap 310 has been inserted into the opening 218 of the base 210. In one example, outer ridges of cap 310 engage internal threads 610 of base 210 to hold cap 310 in place. In another example, snap feet on cap 310 engage mating features of base 210 to hold cap 310 in place. This covers the portion of moveable member 220 remaining in base 210.

In FIG. 8c, skin flap 221 (which would be a scalp flap in neurosurgery) is placed over the surface 304 of the body to cover base 210, cap 310, and the proximal portion of instrument 229. A suitable hole in the skin flap permits the upturned proximal portion of instrument 229 to be exposed outside the skin flap.

Cap Example

FIGS. 9a-9d illustrate one example of cap 310 in detail. In this example, cap 310 includes a relatively larger top 320 and a relatively smaller, generally cylindrical base 330. The exterior of base 330 also has an opening 340 designed to permit the flexible catheter to bend and extend through opening 340 and groove 219 of base 210.

Any means for attaching cap 310 to base 210 is within the scope of the invention. In one example, cap 310 includes a feature that snap-fits into base 210. In another example, the exterior of the base 330 has several circumferential ridges 350 shaped and located to engage internal threads 610 of base 210. In this particular example, the ridges are parallel and thus not external threads that would mate into the internal threads 610 of the base in a manner similar to that of the external threads of the locking ring. However, such a threaded cap is also within the scope of the invention.

Alternative Embodiments

Figure 11A:
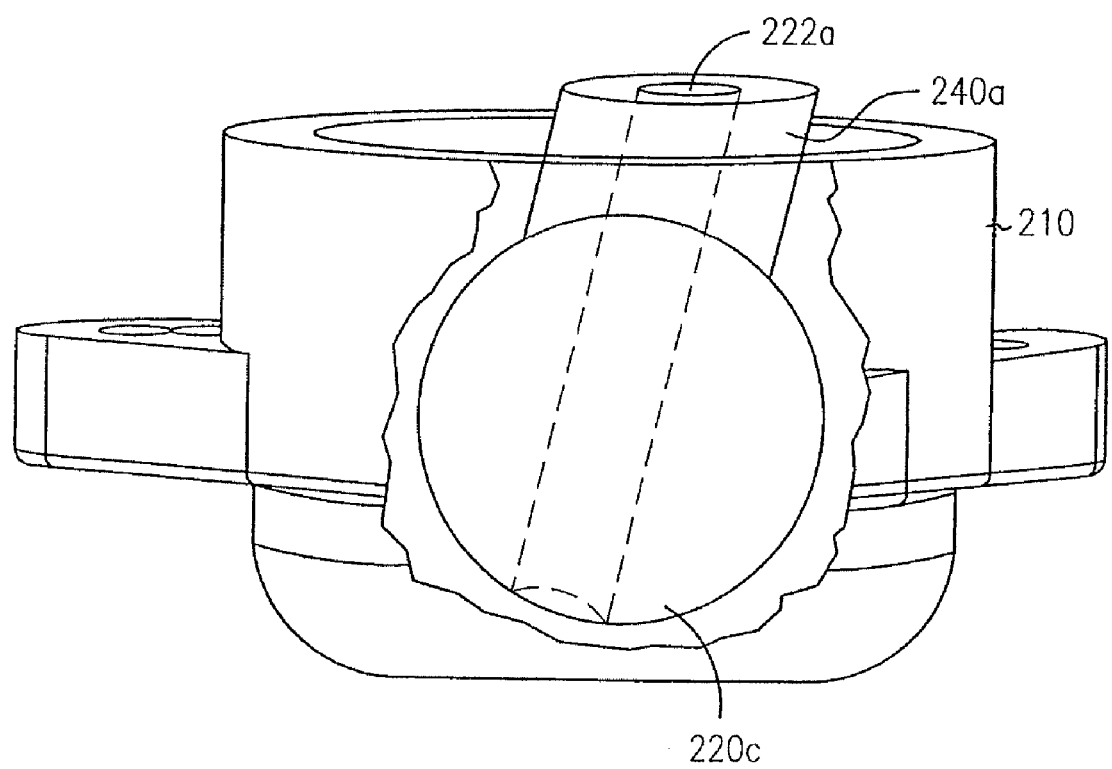
FIG. 11a is a partial cutaway side view of an alternative embodiment of the base and alignment guide.

FIG. 11a shows a modified guide stem 240a, which includes a ball-shaped end 220c located within base 210. Modified guide stem 240a also has an axial opening 222a that is similar in function to axial opening 222 previously described. Modified guide stem 240a may be shorter than previously described guide stem 240 but otherwise functions similarly.

Figure 11B:
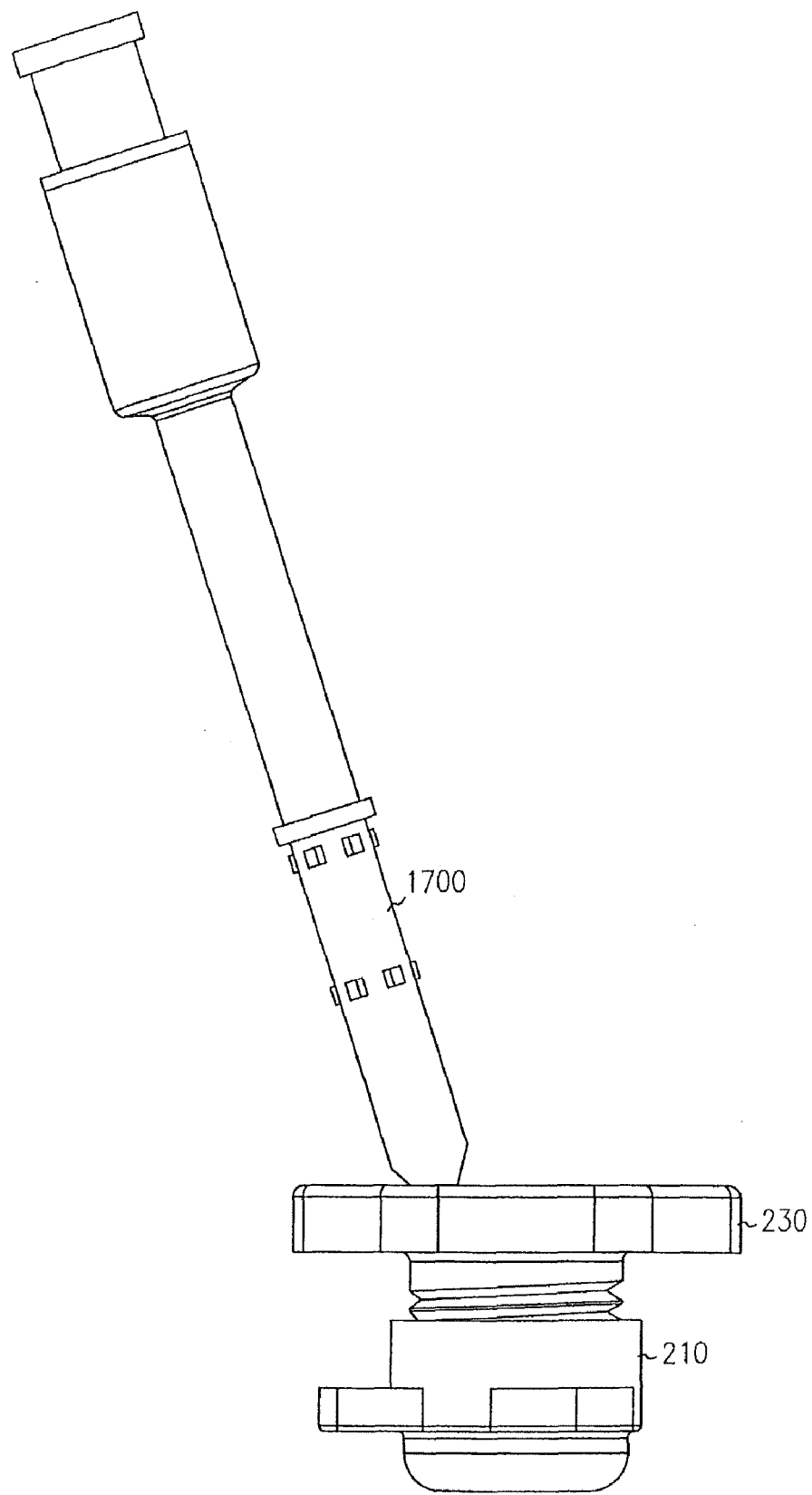
FIG. 11b is a side view illustrating the use of the alternative embodiment of FIG. 11a with the alignment member from FIG. 10.

FIG. 11b illustrates using alignment stem 1700 as described above. Locking ring 230 is used to secure the ball-shaped end 220c within base 210, thereby aligning axial opening 222a as desired. After removal of alignment stem 1700, a catheter is inserted directly into axial opening 222a so that it may be held in place by any convenient means for securing the catheter in place. For example, the diameter of axial opening 222a could be chosen so that, even though ball-shaped end 220c is constructed of a rigid material, friction alone would be adequate to grip the catheter in place yet allow sufficient movement to insert the catheter to the desired position. The catheter is tunneled under the skin as described above; the relatively shorter length of modified guide stem 240a permits the skin flap to cover the base without removal of a relatively longer guide stem 240, as previously described.

Figure 12A:
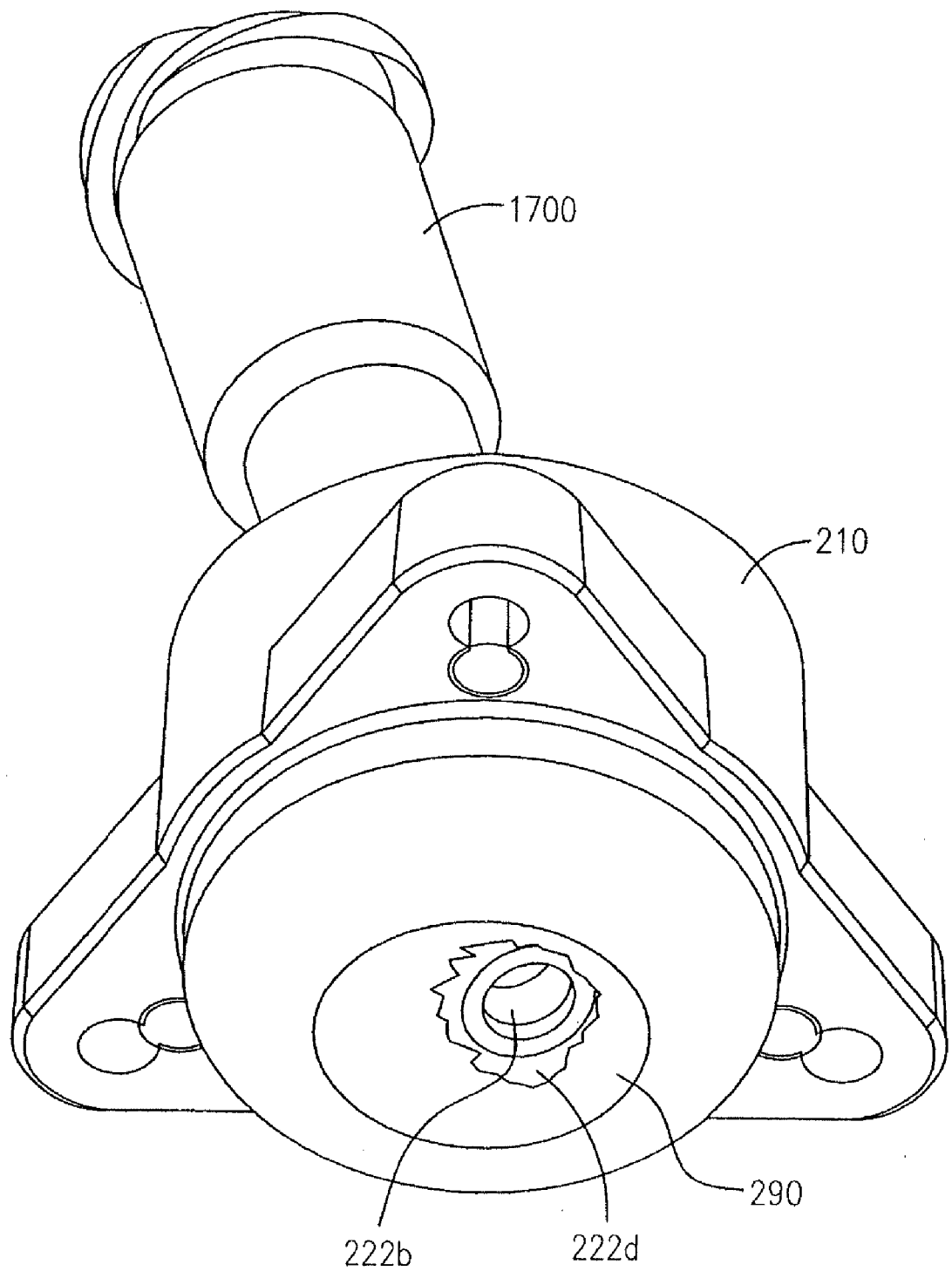
FIG. 12a is a partial cutaway isometric view of yet another alternative embodiment of the base and alignment guide.
Figure 12B:
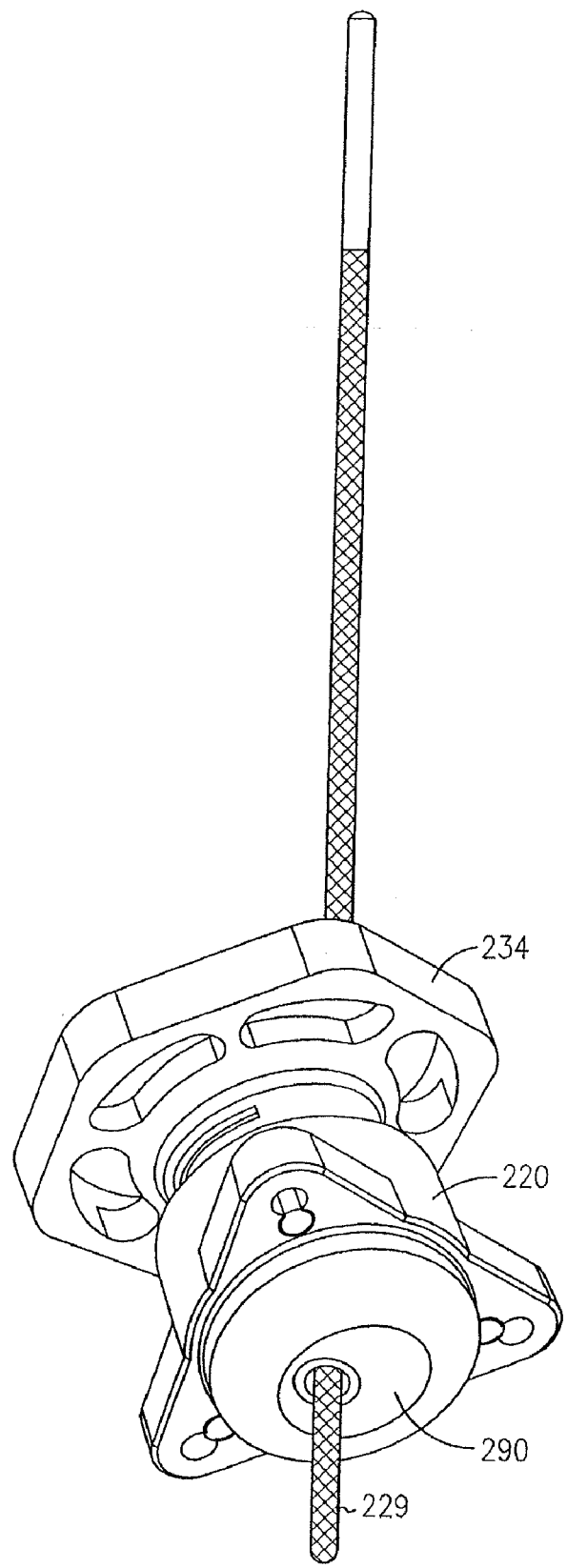
Figure 13A:
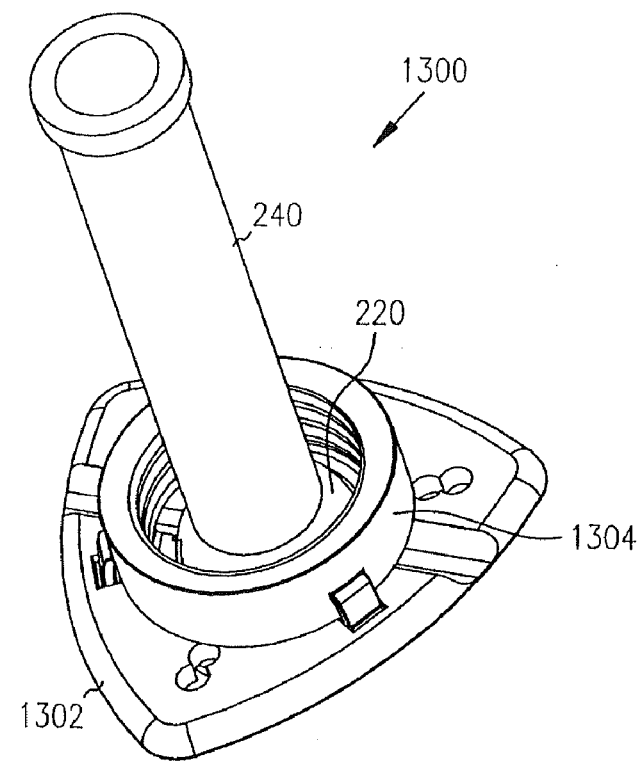
FIG. 13a is a top perspective view of a movable member, a guide stem, and a two-piece base including a mounting seat and a collar.
Figure 13B:
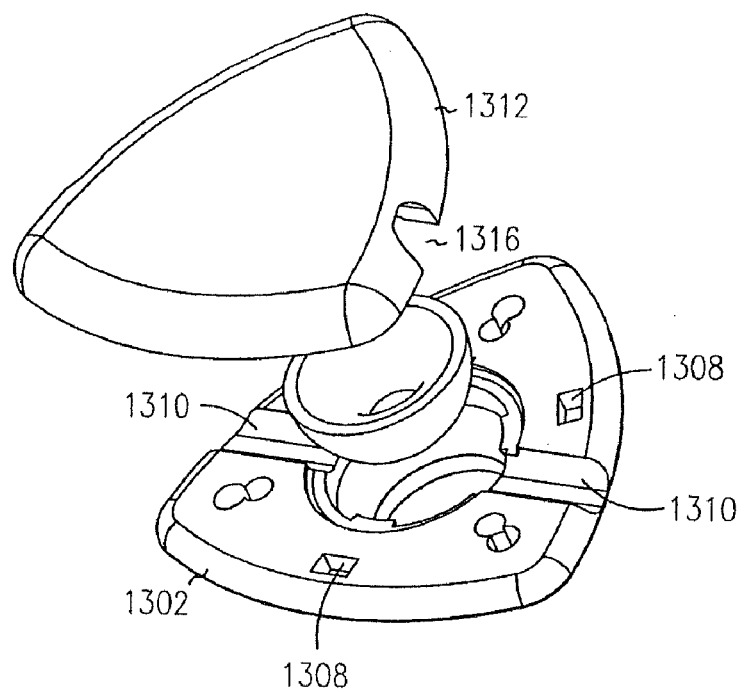
Figure 13C:
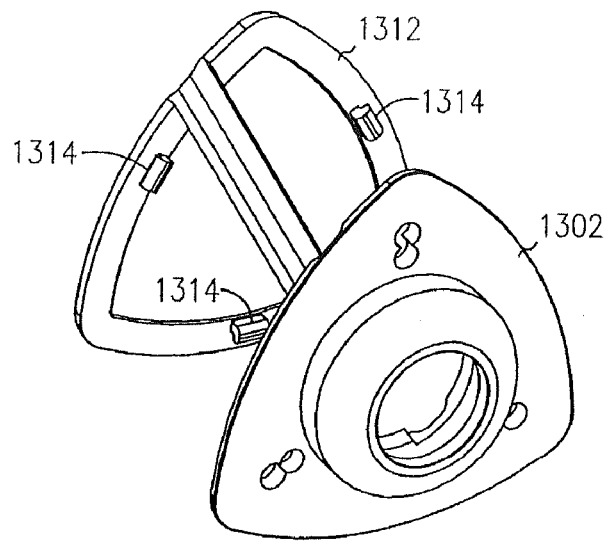
FIG. 13c is a bottom exploded view of the mounting seat and cap of FIG. 13b.
Figure 13D:
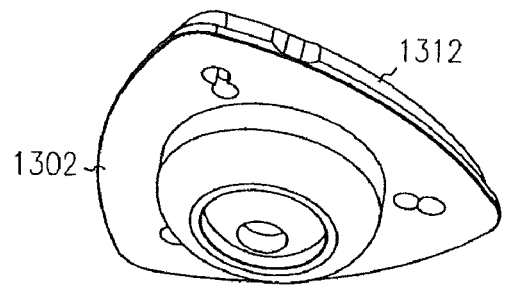
FIG. 13d is a bottom perspective view of the mounting seat and cap of FIG. 13b.
Figure 13E:
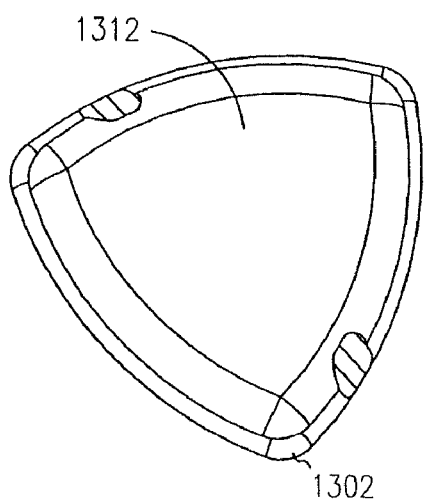
FIG. 13e is a top perspective view of the cap and mounting seat of FIG. 13b.

FIGS. 12a and 12b illustrate schematically still another example within the scope of the invention. FIG. 12a shows alignment stem 1700 and a separate one-piece ball 220d located within base 210. Ball 220d is adapted to engage alignment stem 1700 according to the principles described above. Ball 220d has an axial opening 222b that is similar in function to axial opening 222 of the preferred embodiment. Base 210 also contains alignment material 290 as shown.

Alignment stem 1700 is employed as described above, and locking ring 230 is used to secure ball 220d within the base 210, thereby aligning axial opening 222b as desired. After removal of alignment stem 1700, catheter 229 is inserted directly into axial opening 222a, emerging from the distal outlet and then puncturing through alignment material 290, which secures catheter 229 in place. The catheter is then tunneled under the skin as described above for the preferred embodiment.

The catheters used in the preferred embodiment of neurosurgery typically range in size from 3 to 12 French (1-4 millimeters in diameter). This is small enough that a wide range of materials are suitable for alignment material 290, notably many medical-grade silicones and urethanes.

Yet another variation on this embodiment combines two means for securing the catheter in place. For example, the first means could be either the embodiment of FIGS. 11a and 11b, or the previously described embodiment of a two-piece ball 220 and relaxable stabilizer 227. The second means for securing catheter 229 in place could be the alignment material 290.

Reduced Profile Examples

FIGS. 13a-13e are various views illustrating an alternate example of a two piece version of base 210. Two-piece base 1300 includes a mounting seat 1302 and a collar 1304. In this example, mounting seat 1302 includes a flange with bone screw holes. Mounting seat 1302 also includes a hemispherical recess for receiving a swiveling one or two piece ball-shaped movable member 220. Movable member 220 includes an opening 223 into which a guide stem 240 is threaded. Cylindrical collar 1304 includes internal threads for receiving a locking member 230 for securing movable member 220, after it has been positioned to provide the desired trajectory, while an instrument 280 is inserted through guide stem 240 toward target 270. Collar 1304 includes a coupler, such as legs that detachably snap-fit into receptacles 1308 in base 1302. After instrument 280 is guided to target 270, guide stem 240 is then removed over instrument 280. This allows relaxable stabilizer 227 to hold instrument 280 in place. Locking member 230 and collar 1304 are also then removed. Instrument 280 is bent laterally into a groove 1310 in base 1302. Cap 1312, which includes legs 1314 for snap-fitting into receptacles 1308, is then snapped onto base 1302. Cap 1312 also includes one or more grooves 1316, which aligns with the one or more grooves 1310 in base 1302 for allowing instrument 280 to pass laterally therethrough. This example illustrates how, by separating base 210 into more than one piece (e.g., 1302 and 1304), its profile above the skull may advantageously be reduced by removing one of the pieces (e.g., 1304).

Figure 14A:
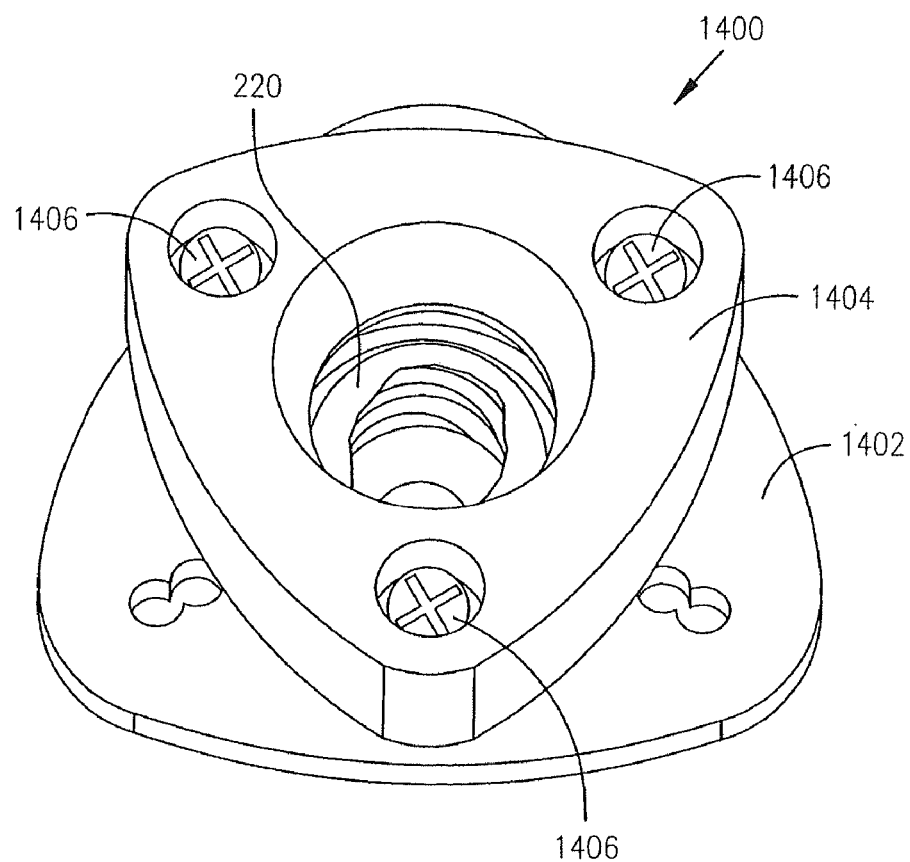
FIG. 14a is a top perspective view of a two-piece base, including a mounting seat and collar, and a movable member.
Figure 14B:
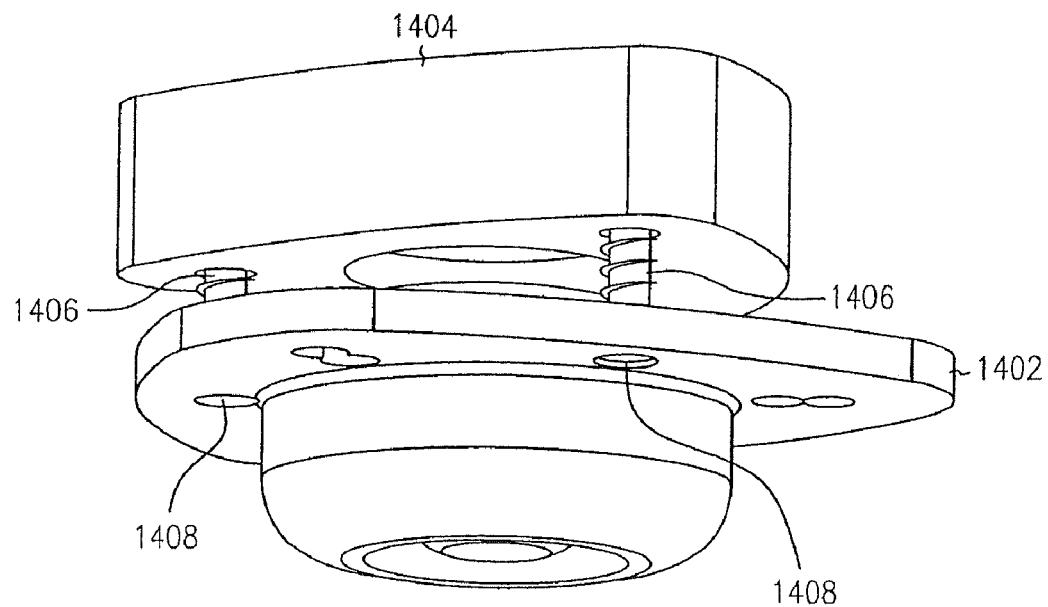

FIGS. 14a-14b are various views illustrating another alternate example of a two piece version of base 210. Two-piece base 1400 includes a mounting seat 1402 and a collar 1404. In this example, mounting seat 1402 includes a flange with bone screw holes. Mounting seat 1402 also includes a hemispherical recess for receiving a swiveling one or two piece ball-shaped movable member 220. Movable member 220 includes an opening 223 into which a guide stem 240 is threaded. Cylindrical collar 1404 includes internal threads for receiving a locking member 230 for securing movable member 220, after it has been positioned to provide the desired trajectory, while an instrument 280 is inserted through guide stem 240 toward target 270. Collar 1404 includes a coupler, such as countersunk holes for receiving screws 1406 that detachably engage internally threaded receptacles 1408 in base 1402. This example illustrates how, by separating base 210 into more than one piece (e.g., 1402 and 1404), its profile above the skull may advantageously be reduced by removing one of the pieces (e.g., 1404).

Figure 15A:
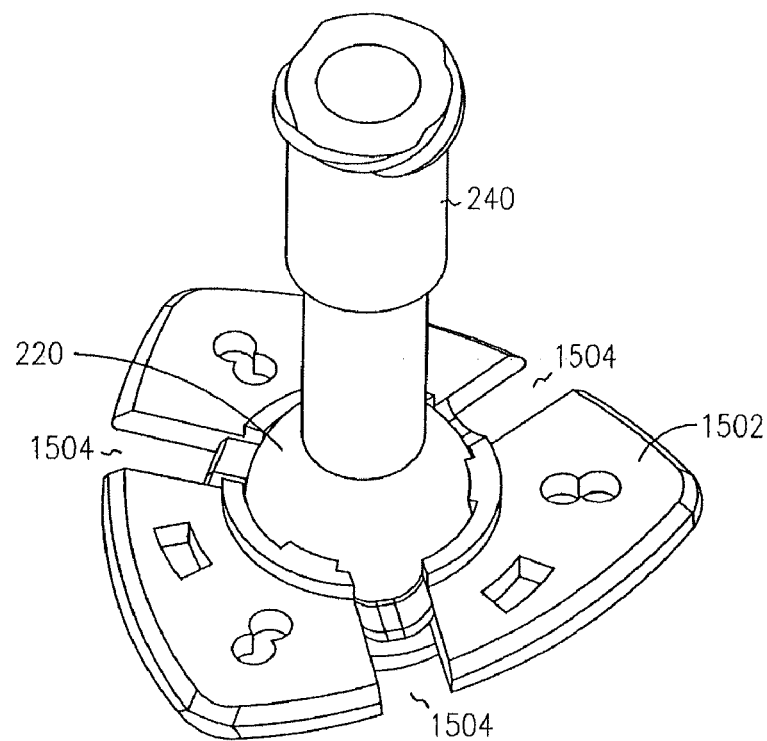
FIG. 15a is a top perspective view of a low-profile mounting seat, movable member and guide stem.
Figure 15B:
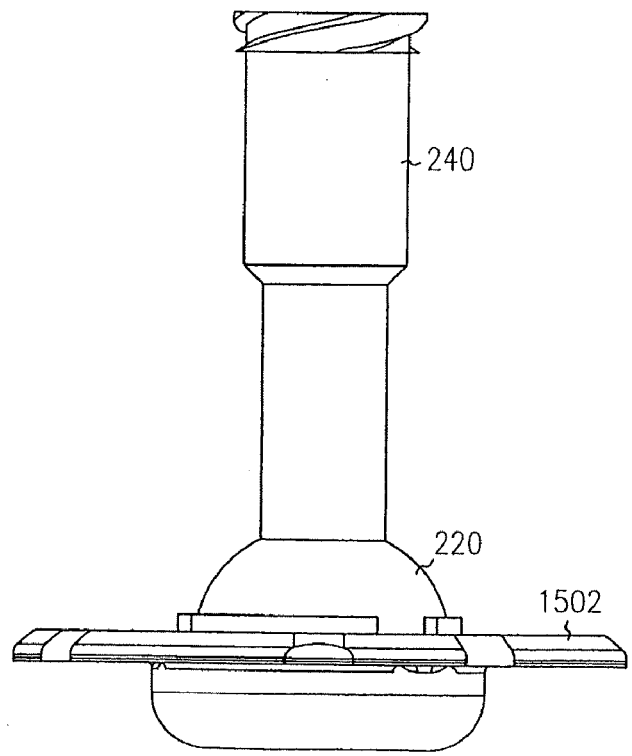

FIGS. 15a and 15b are various views illustrating another example of a low profile mounting seat 1502, to which a removable internally threaded collar can be snap-fit, along with a movable member 220 and guide stem 240. This example includes three grooves 1504 into which an instrument 280 can be laterally bent. A matching cap with an aligning groove is then snap-fitted into the receptacles.

Figure 16A:
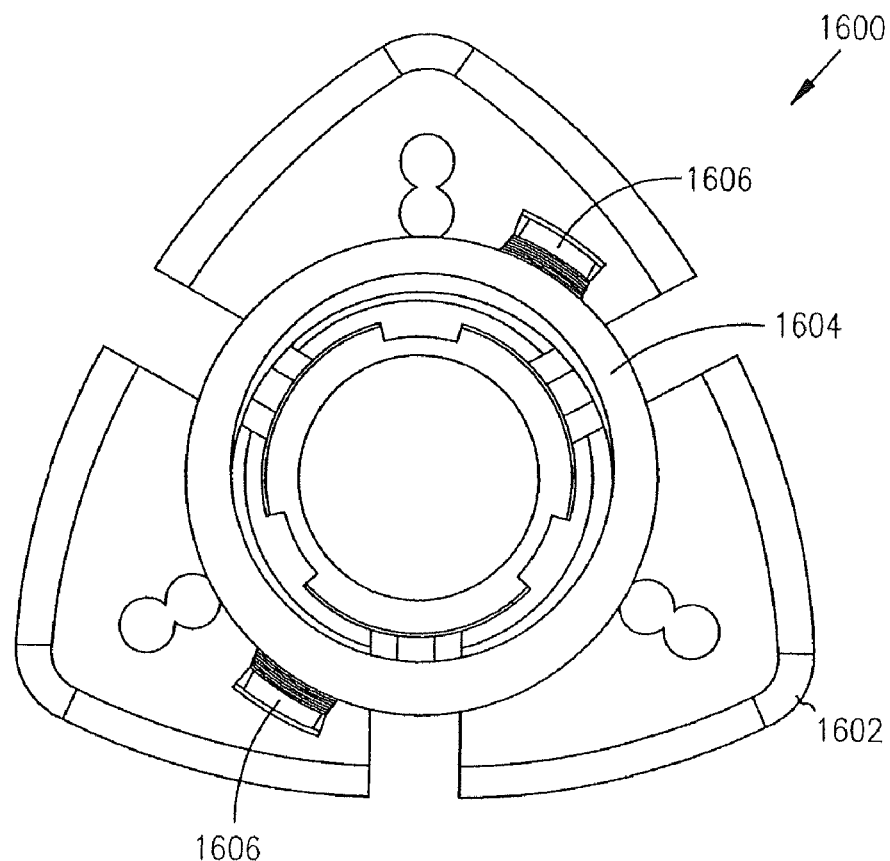
FIG. 16a is a top view of a low-profile mounting seat, movable member, and collar.
Figure 16B:
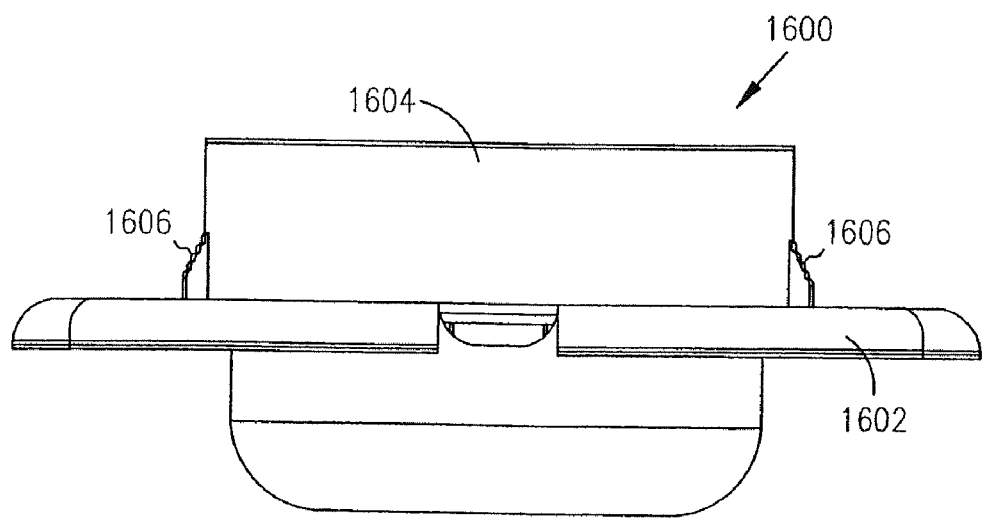
Figure 16C:
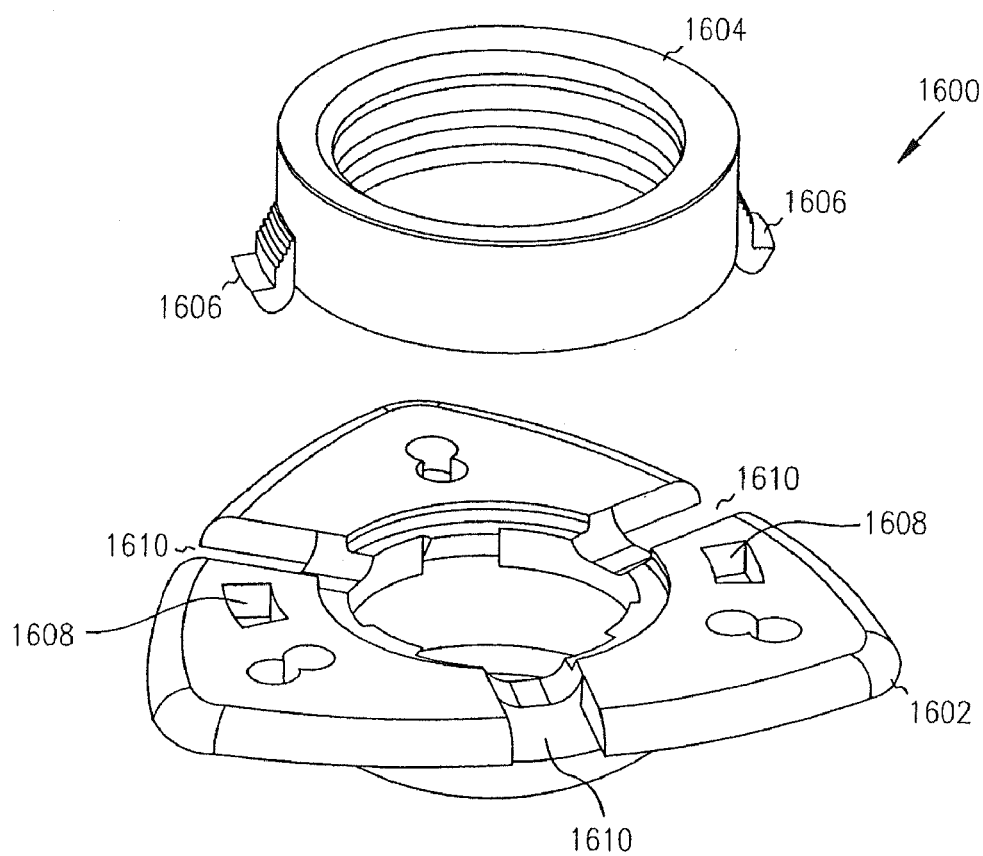
FIG. 16c is a top exploded view of the two-piece base provided by the mounting seat and collar of FIGS. 16a and 16b.
Figure 17:
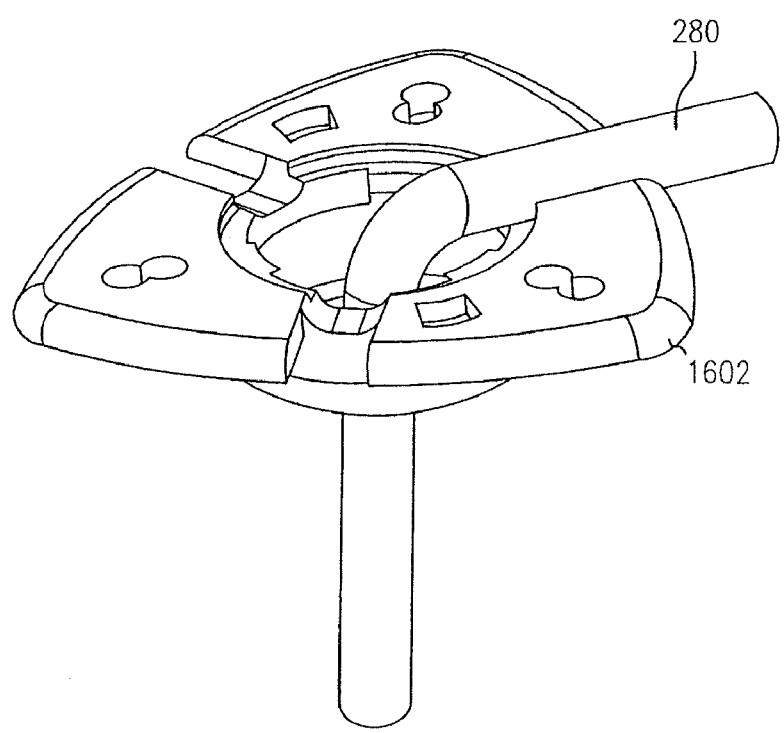
FIG. 17 is a top perspective view illustrating an example of an instrument that has been laterally bent into one of the grooves of the mounting seat of FIGS. 16a-16c.

FIGS. 16a-16c are various views illustrating another example of a two-piece base 1600 including a mounting seat 1602, a removable internally-threaded collar 1604, and a movable member 220. This example of mounting seat 1602 includes three grooves 1604 into which an instrument 280 can be laterally bent after removing collar 1604. In this example, collar 1604 includes a coupler, such as attachment feet 1606 that are pushed toward each other by the user in order to snap collar 1604 into and out of receptacles 1608 in mounting seat 1602. This example also includes three grooves 1610 into which an instrument 280 can be laterally bent after removing collar 1604, as illustrated in FIG. 17. A matching cap with an aligning groove is then snap-fitted into the receptacles 1608.

Figure 18A:
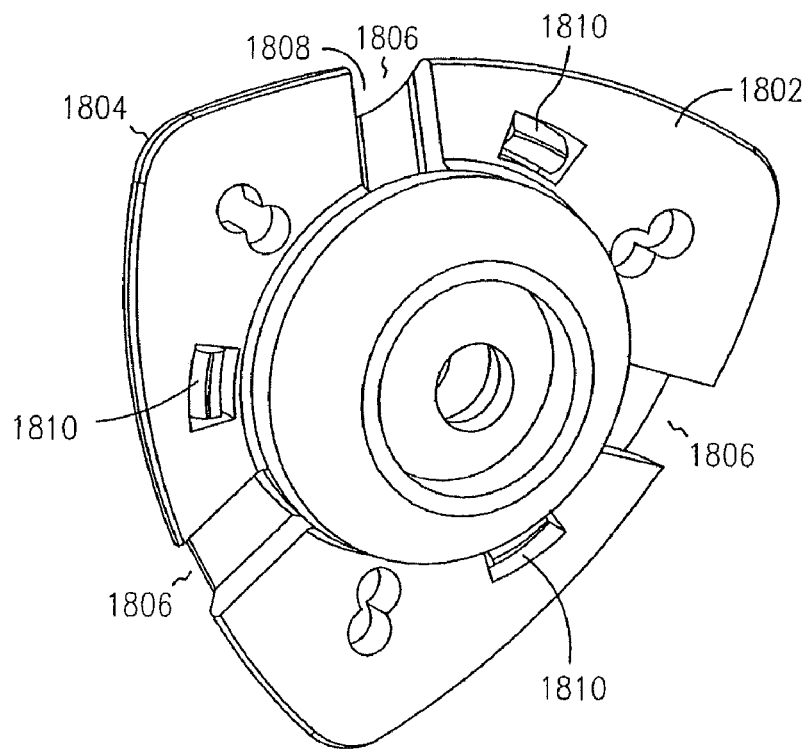
FIG. 18a is a bottom perspective view of an example of a low-profile mounting seat and cap.
Figure 18B:
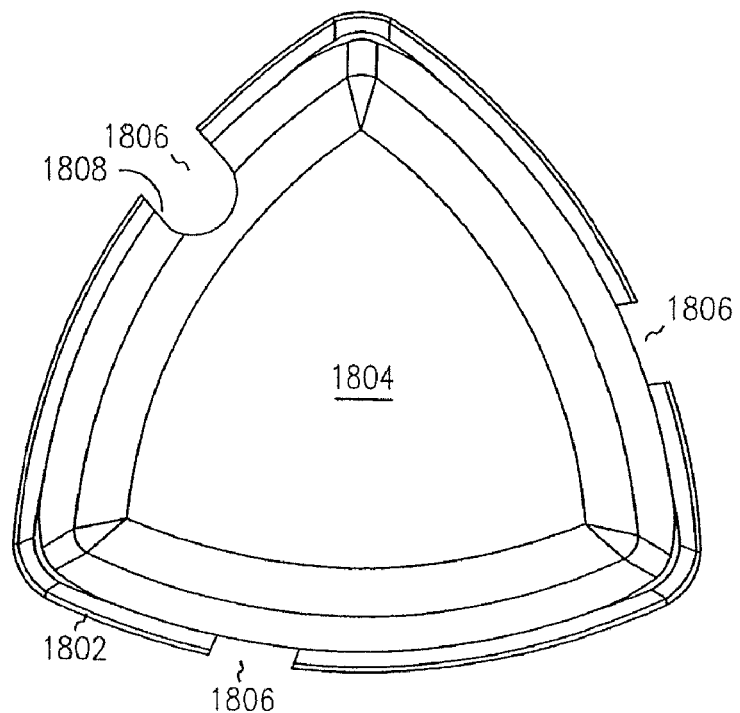
Figure 18C:
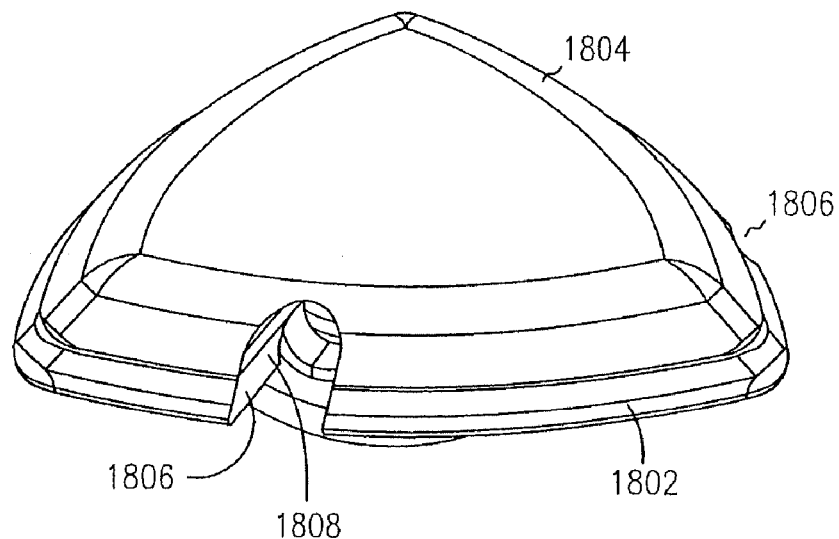
FIG. 18c is a side perspective view of the cap and mounting seat of FIGS. 18a and 18b.

FIGS. 18a-18c are various views illustrating an alternate example of a low-profile mounting seat 1802 portion of a two-piece base and a cap 1804. In this example, mounting seat 1802 includes three grooves 1806 into which an instrument 280 can be laterally bent. Cap 1804 includes a single groove 1808 that is aligned, by rotating cap 1804 with respect to mounting seat 1802 before snap-fitting it thereto, to the groove in mounting seat 1802 into which instrument 280 has been laterally bent. Three feet in cap 1804 align with matching receptacles 1810 in mounting seat 1802 so that groove 1808 in cap 1804 is capable of being aligned with any of the grooves 1806 in mounting seat 1802.

Stabilizer Sliding Cap Example

Figure 19A:
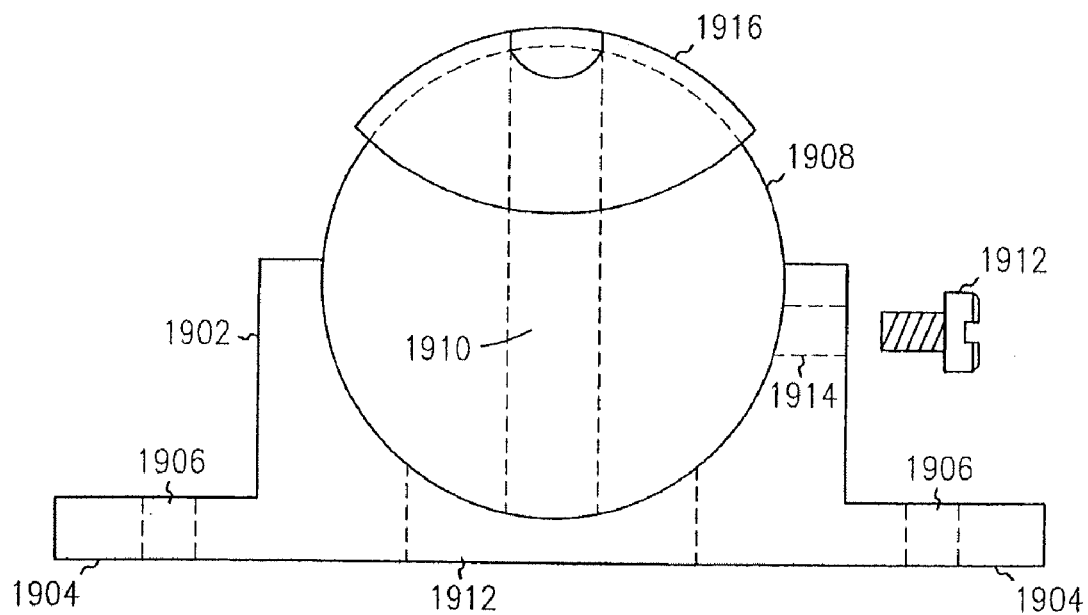
FIG. 19a is a side view of a mounting seat, ball, and stabilizing cap.
Figure 19B:
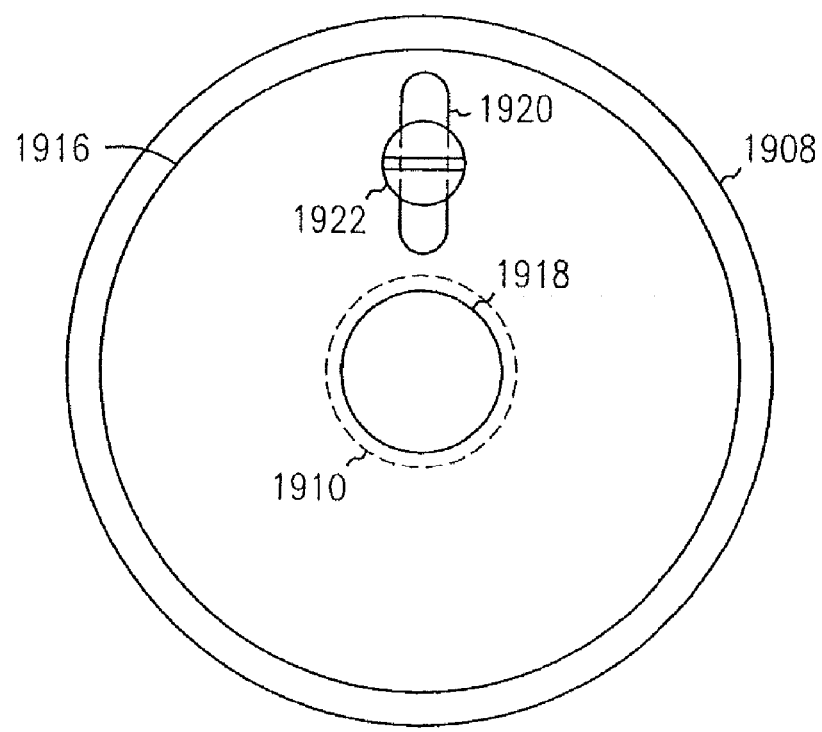
FIG. 19b is a top view of the ball and cap with aligned openings.
Figure 19C:
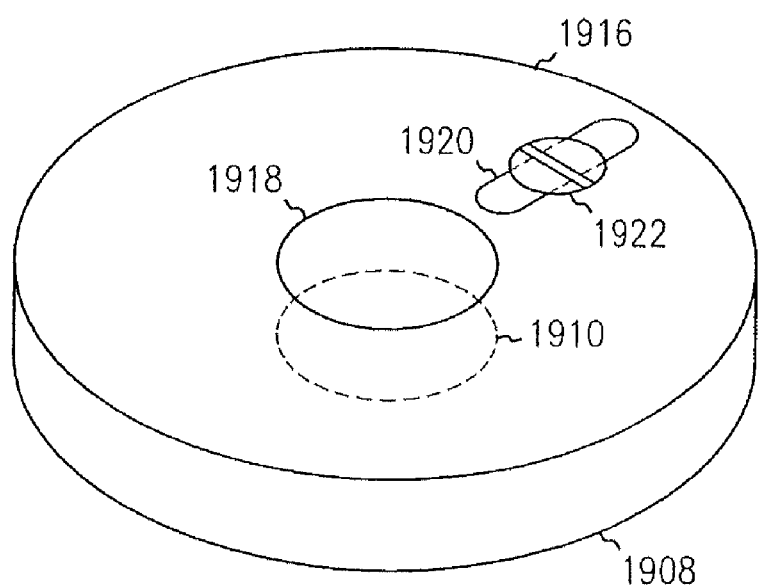
FIG. 19c is a top view of the ball and cap with offset openings to grasp and stabilize an instrument.

FIGS. 19*a*-*c* are various views illustrating an alternative example capable of using a cap or other slide component to stabilize a catheter or other medical instrument. FIG. 19*a* is a side view of a mounting seat 1902 with laterally extending flanges 1904 that include bone screw openings 1906. A hemispherical seat portion of mounting seat 1902 receives a one-piece ball 1908 with a trajectory passage 1910 extending therethrough. The hemispherical seat portion of mounting seat 1902 also includes an opening 1912 that aligns with passage 1910 as ball 1908 is swiveled within mounting seat 1902 by manipulating a guide stem that is threaded into passage 1910 as discussed above. In this example, a set screw locking member 1912 is inserted through an opening 1914 in mounting seat 1902 to secure ball 1908 in place after the desired position has been obtained. A hemispherically conformal cap 1916 is situated about the top of ball 1908. FIG. 19*b* is a top view illustrating opening 1918 being concentrically aligned to the top opening of passage 1910 through ball 1908. As shown in FIG. 19*b*, the passage 1910 can have a width (e.g., diameter) that is greater than a width (e.g., diameter) of the opening 1918. Cap 1916 also includes a slot 1920 through which set screw 1922 passes. Set screw 1922 engages an underlying threaded opening on the top surface of ball 1908. FIG. 19*c* is a top view illustrating how cap 1916 can be slid along ball 1908 in the direction of slot 1920 to offset opening 1918 in cap 1916 from the top opening of passage 1910 in ball 1908. This reduces the effective area of passage 1910 through which a catheter or other instrument has been passed. By tightening set screw 1922, cap 1916 is used to grasp and stabilize the catheter or other instrument through passage 1910. Cap 1916 is any rigid, semi-rigid, relaxable, or flexible material (or combination thereof) suitable for grasping and stabilizing an instrument by narrowing the effective cross-sectional area of passage 1910, e.g., by offsetting the opening 1918 of cap 1916.

Other Aspects

The invention as described above can be used with various known aspects of remote actuation systems, perhaps with minor modifications to accommodate the features of the invention that would be within the ordinary skill of the art. Suitable examples are the mechanical and hydraulic remote actuation and control devices taught in the International Patent Application cited above. Similarly, mechanisms to laterally displace the apparatus without changing the trajectory of the catheter or instrument held by the relaxable stabilizer in the movable member may be employed. An example would be the stage mechanism taught in the same International Patent Application. Any suitable system for computerized monitoring and/or control of the invention may be employed.

Other Uses

The invention can be practiced in conjunction with trajectory guides adapted for various parts of the body, including uses related to biopsies or therapy provided to organs in or near the abdomen or pelvis. Among the uses are liver biopsies, renal biopsies, pancreatic biopsies, adrenal biopsies. In addition, some procedures require both a biopsy as well as a therapy. The biopsy needle is used first and then an instrument used in therapy is substituted for the biopsy needle. The instrument for applying therapy includes instruments for thermal ablation, and instruments for providing shunts to various organs such as TIPS (transjugular interhepatic portal systemic shunts). The inventive trajectory guide can also be used to conduct biliary drainages, and used to conduct other biopsies and treatments at or near the abdomen of the pelvis. The trajectory guide can also be used for procedures on the back and near the spine of a patient. Nerve blocks, epidural injections, facet injections, sacroiliac joint injections, and spinal cordotomy are just a few of the procedures possible with the trajectory guide. Non-brain treatments and biopsies in the head and neck can also be accomplished using the trajectory guide. Trigeminal neuralgia can be treated using the trajectory guide. Biopsies of the pleura, the lung, and the mediastinum and removal of emphysematous to reduce the volume of the lung can be done percutaneously using the trajectory guide. The trajectory guide can also be used for fetal surgery such as for diversion of fetal hydrocephalus, and for treatment of fetal hydronephrosis. These are just a sampling of the possible procedures that can be done using the body portal type trajectory guide. Numerous other procedures will be accomplished using this device. In addition, the device will give rise to other future surgical procedures.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A trajectory guide assembly that guides an instrument relative to a patient, the trajectory guide assembly comprising:
   a mounting seat configured to be supported by the patient;
   a trajectory member moveably supported by the mounting seat, the trajectory member defining a trajectory passage; and
   a cap member moveably supported by the trajectory member, the cap member defining a cap opening, the cap member selectively moveable to a first position relative to the trajectory member to retain the instrument in a fixed position relative to both the cap opening and the trajectory passage, and the cap member selectively moveable to a second position relative to the trajectory member to release the instrument, wherein the cap opening is misaligned with the trajectory passage when in the first position, and wherein the cap opening is aligned with the trajectory passage when in the second position.

2. The trajectory guide assembly of claim 1, wherein the cap member is selectively securable in a fixed position relative to the trajectory member.

3. The trajectory guide assembly of claim 2, further comprising a set screw, wherein the cap member defines a slot and the set screw extends through the slot and is selectively securable to the trajectory member, the set screw moveable relative to the slot to limit movement of the cap member relative to the trajectory member.

4. The trajectory guide assembly of claim 1, wherein the trajectory member is selectively securable in a fixed position relative to the mounting seat.

5. The trajectory guide assembly of claim 4, further comprising a set screw that extends through the mounting seat and is selectively securable to the trajectory member.

6. The trajectory guide assembly of claim 1, wherein the trajectory member is spherical, and the mounting seat includes a hemispherical seat portion that receives the trajectory member, the trajectory member rotatably moveable within the hemispherical seat portion.

7. The trajectory guide assembly of claim 1, wherein the trajectory member is spherical, and the cap member is a hemispherically conformed cap member that receives the trajectory member.

8. The trajectory guide assembly of claim 1, wherein the mounting seat defines a seat opening, wherein the seat opening of the mounting seat, the trajectory passage, and the cap opening of the cap member are able to simultaneously receive the instrument.

9. The trajectory guide assembly of claim 8, wherein the seat opening in the mounting seat has a width that is greater than a width of the trajectory passage.

10. A trajectory guide assembly that guides an instrument relative to a patient, the trajectory guide assembly comprising:
    a mounting seat configured to be supported by the patient;
    a trajectory member moveably supported by the mounting seat, the trajectory member defining a trajectory passage; and
    a cap member moveably supported by the trajectory member, the cap member defining a cap opening, the cap member selectively moveable to a first position relative to the trajectory member to retain the instrument in both the cap opening and the trajectory passage, and the cap member selectively moveable to a second position relative to the trajectory member to release the instrument, wherein the trajectory passage has a width that is greater than a width of the cap opening in the cap member.

11. The trajectory guide assembly of claim 1, wherein the mounting seat includes a flange that is selectively fixable to the patient.

12. The trajectory guide assembly of claim 1, wherein the cap member is slidably supported by the trajectory member.

13. A trajectory guide assembly that guides an instrument relative to a patient, the trajectory guide assembly comprising:
    a mounting seat configured to be supported by the patient, the mounting seat including a hemispherical seat portion defining a seat opening passing therethrough;
    a ball member rotatably supported within the hemispherical seat portion, the ball member defining a trajectory passage, the trajectory passage and the seat opening configured to simultaneously receive the instrument; and
    a cap member that is moveably supported by the ball member, the cap member defining a cap opening, wherein the cap member is selectively moveable to a first position relative to the ball member to retain the instrument in a fixed position relative to each of the cap opening, the trajectory passage, and the seat opening, and the cap member is selectively moveable to a second position relative to the ball member to release the instrument, wherein the cap member is slidable from the first position to the second position, when in the first position the cap opening is offset from the trajectory passage, and when in the second position the cap opening is concentric with the trajectory passage.

14. The trajectory guide assembly of claim 13, further comprising a set screw, wherein the cap member defines a slot, and the set screw extends through the slot and is selectively securable to the ball member, the set screw moveable relative to the slot to limit movement of the cap member relative to the ball member.

15. The trajectory guide assembly of claim 13, wherein the ball member is selectively securable in a fixed position relative to the hemispherical seat portion.

16. The trajectory guide assembly of claim 13, wherein the ball member is a one-piece ball member.

17. The trajectory guide assembly of claim 13, wherein the cap member includes a hemispherical cap that is disposed on a top of the ball member.

18. A method for guiding an instrument relative to a patient comprising:
    positioning a mounting seat on the patient;
    positioning a trajectory member on the mounting seat;
    rotating the trajectory member relative to the mounting seat to point an axis of a trajectory passage toward a target in the patient;
    moving a cap member relative to the trajectory member to expose the trajectory passage through an opening in the cap member and to align the opening in the cap member with the trajectory passage;
    introducing the instrument through the opening in the cap member, the trajectory passage, and into the patient toward the target; and
    moving the cap member relative to the trajectory member to misalign the opening in the cap member from the trajectory passage to retain the instrument in a fixed position relative to both the opening and the trajectory passage and between the cap member and the trajectory member.

19. A trajectory guide assembly that guides an instrument relative to a patient, the trajectory guide assembly comprising:
    a mounting seat configured to be supported by the patient, the mounting seat including a flange, the flange defining a hole that receives a fastener for selectively securing the mounting seat to the patient, the mounting seat further including a hemispherical seat portion that defines a seat opening;
    a spherical ball member rotatably supported within the hemispherical seat portion, the ball member defining a trajectory passage, the trajectory passage having a width that is less than a width of the seat opening;
    a first set screw that extends through the mounting seat and selectively secures the spherical ball member in a fixed position relative to the mounting seat;
    a cap member that is slidably supported by the ball member, the cap member defining a cap opening and a slot, the cap opening having a width that is less than a width of the trajectory passage; and
    a second set screw that is moveably received in the slot and that selectively secures the cap member in a fixed position relative to the ball member, the slot limiting movement of the cap member relative to the ball member, the cap member selectively moveable to a first position relative to the ball member to retain the instrument in each of the seat opening, the trajectory passage, and the cap opening and between the cap member and the trajectory member, the cap member selectively moveable to a second position relative to the ball member to release the instrument.

* * * * *